(12) United States Patent
Pierce et al.

(10) Patent No.: US 11,673,869 B2
(45) Date of Patent: *Jun. 13, 2023

(54) 4-OXAZOLIDINONE ANTIMICROBIAL AGENTS

(71) Applicant: NORTH CAROLINA STATE UNIVERSITY, Raleigh, NC (US)

(72) Inventors: Joshua G. Pierce, Raleigh, NC (US); Jonathan J. Mills, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 1 day.

This patent is subject to a terminal disclaimer.

(21) Appl. No.: 17/101,722

(22) Filed: Nov. 23, 2020

(65) Prior Publication Data

US 2021/0323934 A1 Oct. 21, 2021

Related U.S. Application Data

(63) Continuation of application No. 16/327,478, filed as application No. PCT/US2017/048034 on Aug. 22, 2017, now Pat. No. 10,844,025.

(60) Provisional application No. 62/378,171, filed on Aug. 22, 2016.

(51) Int. Cl.
| | |
|---|---|
| *C07D 263/40* | (2006.01) |
| *C07D 263/46* | (2006.01) |
| *A61P 31/04* | (2006.01) |
| *A01N 43/76* | (2006.01) |
| *A61L 31/16* | (2006.01) |
| *A61L 29/16* | (2006.01) |
| *A61L 27/54* | (2006.01) |
| *A61L 31/08* | (2006.01) |

(52) U.S. Cl.
CPC .......... *C07D 263/40* (2013.01); *A01N 43/76* (2013.01); *A61L 27/54* (2013.01); *A61L 29/16* (2013.01); *A61L 31/08* (2013.01); *A61L 31/16* (2013.01); *A61P 31/04* (2018.01); *C07D 263/46* (2013.01); *A61L 2300/204* (2013.01); *A61L 2300/404* (2013.01)

(58) Field of Classification Search
None
See application file for complete search history.

(56) References Cited

U.S. PATENT DOCUMENTS 10,844,025 B2 * 11/2020 Pierce ................. A61L 31/16

* cited by examiner

*Primary Examiner* — Brian J Davis
(74) *Attorney, Agent, or Firm* — Meunier Carlin & Curfman LLC

(57) ABSTRACT

Provided herein are oxazolidinone derivatives that can exhibit anti-microbial activity and/or activity as biofilm modulating agents (e.g., activity as biofilm inhibitors and/or activity as biofilm dispersal agents). The compounds can exhibit potent activity anti-microbial activity (e.g., potent activity against Gram-positive positive bacteria including methicillin-resistant *Staphylococcus aureus*). The compounds can exhibit potent activity against biofilms. In some cases, the compounds can exhibit both anti-microbial activity and biofilm modulation properties.

11 Claims, No Drawings

4-OXAZOLIDINONE ANTIMICROBIAL AGENTS

CROSS REFERENCE TO RELATED APPLICATIONS

This application claims the benefit of U.S. Provisional Application No. 62/378,171, filed Aug. 22, 2016, which is incorporated herein by reference in its entirety.

STATEMENT REGARDING FEDERALLY SPONSORED RESEARCH OR DEVELOPMENT

This invention was made with Government Support under Grant No. GM110154 awarded by the National Institutes of Health. The Government has certain rights in the invention.

BACKGROUND

Infectious diseases caused, for example, by bacteria are becoming increasingly difficult to treat and cure. In particular, the emerging resistance of pathogenic bacteria to antibiotics that find use in medicinal application poses a serious health challenge. The identification of antibiotic resistant microbes such as methicillin-resistant *Staphylococcus aureus* (MRSA), fluoroquinolone resistant *Pseudomonas aeruginosa, Clostridium difficile*, and multi-drug resistant *Salmonella* spp. represent a few notable examples of this emerging problem. The rate of discovery and approval of new antimicrobial agents does not match the rate at which antibiotics in use tend to lose efficacy. This discrepancy makes it urgent to search for new potent and safe antimicrobial agents.

Accordingly, there is a need to identify and develop new and anti-microbial agents to treat infectious disease.

SUMMARY

Provided herein are oxazolidinone derivatives that can exhibit anti-microbial activity and/or activity as biofilm modulating agents (e.g., activity as biofilm inhibitors and/or activity as biofilm dispersal agents). The compounds can exhibit potent activity anti-microbial activity (e.g., potent activity against Gram-positive positive bacteria including methicillin-resistant *Staphylococcus aureus*). The compounds can exhibit potent activity against biofilms. In some cases, the compounds can exhibit both anti-microbial activity and biofilm modulation properties.

Provided herein are compounds defined by Formula I

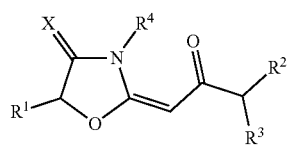

Formula I or a pharmaceutically acceptable salt or prodrug thereof, wherein X is chosen from O and S; $R^1$ is chosen from hydrogen, halogen, hydroxyl, —CN, —NO$_2$, amino, alkylamino, dialkylamino, alkyl, haloalkyl, alkylthio, haloalkylthio, alkoxy, haloalkoxy, alkenyl, haloalkenyl, alkynyl, haloalkynyl, aryl, heteroaryl, cycloalkyl, cycloheteroalkyl, alkylaryl, alkylheteroaryl, alkylcycloalkyl, alkylcycloheteroalkyl, alkylsulfinyl, haloalkylsulfinyl, alkyl sulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, dialkylaminocarbonyl, and heterodialkylaminocarbonyl, each optionally substituted with one or more substituents individually chosen from $R^5$; $R^2$ is chosen from alkylamino, dialkylamino, alkyl, haloalkyl, alkynyl, haloalkynyl, alkylthio, haloalkylthio, alkoxy, haloalkoxy, aryl, heteroaryl, cycloalkyl, cycloheteroalkyl, alkyl aryl, alkylheteroaryl, alkylcycloalkyl, and alkylcycloheteroalkyl, each optionally substituted with one or more substituents individually chosen from $R^5$; $R^3$ is chosen from hydrogen, halogen, hydroxyl, —CN, —NO$_2$, amino, alkylamino, dialkylamino, alkyl, haloalkyl, alkynyl, haloalkynyl, alkylthio, haloalkylthio, alkoxy, haloalkoxy, aryl, heteroaryl, cycloalkyl, cycloheteroalkyl, alkylaryl, alkylheteroaryl, alkyl cycloalkyl, alkylcycloheteroalkyl alkylsulfinyl, haloalkylsulfinyl, alkyl sulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, dialkylaminocarbonyl, and heterodialkylaminocarbonyl, each optionally substituted with one or more substituents individually chosen from $R^5$; $R^4$ is chosen from hydrogen, alkyl, haloalkyl, alkylthio, haloalkylthio, alkenyl, haloalkenyl, alkynyl, haloalkynyl, aryl, heteroaryl, cycloalkyl, cycloheteroalkyl, alkyl aryl, alkylheteroaryl, alkylcycloalkyl, and alkylcycloheteroalkyl, each optionally substituted with one or more substituents individually chosen from $R^5$; and $R^5$ is chosen from hydroxy, halogen, —CN, —NO$_2$, amino, alkylamino, dialkylamino, alkyl, haloalkyl; alkylthio; haloalkylthio; alkoxy, haloalkoxy, alkenyl, haloalkenyl, alkynyl, haloalkynyl, aryl, heteroaryl, cycloalkyl, cycloheteroalkyl, alkylaryl, alkylheteroaryl, alkylcycloalkyl, alkyl cycloheteroalkyl, alkylsulfinyl, haloalkylsulfinyl, alkyl sulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, dialkylaminocarbonyl, and heterodialkylaminocarbonyl.

In some embodiments, X can be O. In other embodiments, X can be S.

In some embodiments, $R^1$ can comprise an alkyl group (e.g., a branched alkyl group). In some embodiments, $R^1$ can comprise a $C_1$-$C_4$ alkyl group (e.g., a $C_2$-$C_4$ alkyl group). In certain embodiments, $R^1$ can comprise a $C_3$-$C_4$ alkyl group (e.g., a branched $C_3$-$C_4$ alkyl group, such as an isopropyl group). In other embodiments, $R^1$ can comprise an aryl group or an alkylaryl group. For example, $R^1$ can be a substituted or unsubstituted phenyl group or a substituted or unsubstituted benzyl group.

In some embodiments, $R^3$ can be hydrogen. In other embodiments, $R^3$ can comprise an alkyl group, an aryl group, or an alkylaryl group. For example, in some cases, $R^3$ is can be a substituted or unsubstituted aryl group (e.g., substituted or unsubstituted phenyl group or a substituted or unsubstituted benzyl group).

In some embodiments, $R^2$ can be hydrogen. In other embodiments, $R^2$ can comprise an alkyl group, an aryl group, or an alkylaryl group.

In some embodiments, $R^4$ is hydrogen. In other embodiments, $R^4$ can comprise an alkyl group, an aryl group, or an alkylaryl group. For example, $R^4$ can be a substituted or unsubstituted aryl group (e.g., substituted or un substituted phenyl group or a substituted or unsubstituted benzyl group) or a substituted or unsubstituted $C_1$-$C_4$ alkyl group.

In some embodiments, the compound can be defined by Formula II

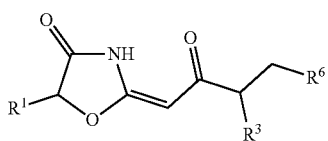

Formula II or a pharmaceutically acceptable salt or prodrug thereof, wherein $R^1$ is chosen from hydrogen, halogen, hydroxyl, —CN, —NO$_2$, amino, alkylamino, dialkylamino, alkyl, haloalkyl, alkylthio, haloalkylthio, alkoxy, haloalkoxy, alkenyl, haloalkenyl, alkynyl, haloalkynyl, aryl, heteroaryl, cycloalkyl, cycloheteroalkyl, alkylaryl, alkylheteroaryl, alkylcycloalkyl, alkyl cycloheteroalkyl, alkyl sulfinyl, haloalkylsulfinyl, alkyl sulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, dialkylaminocarbonyl, and heterodialkylaminocarbonyl, each optionally substituted with one or more substituents individually chosen from $R^5$; $R^3$ is chosen from hydrogen, halogen, hydroxyl, —CN, —NO$_2$, amino, alkylamino, dialkylamino, alkyl, haloalkyl, alkynyl, haloalkynyl, alkylthio, haloalkylthio, alkoxy, haloalkoxy, aryl, heteroaryl, cycloalkyl, cycloheteroalkyl, alkylaryl, alkylheteroaryl, alkylcycloalkyl, alkyl cycloheteroalkyl alkyl sulfinyl, haloalkylsulfinyl, alkyl sulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, dialkylaminocarbonyl, and heterodialkylaminocarbonyl, each optionally substituted with one or more substituents individually chosen from $R^5$; $R^6$ is chosen from hydrogen, halogen, hydroxyl, —CN, —NO$_2$, amino, alkylamino, dialkylamino, alkyl, haloalkyl, alkenyl, haloalkenyl, alkynyl, haloalkynyl, alkylthio, haloalkylthio, alkoxy, haloalkoxy, aryl, heteroaryl, cycloalkyl, cycloheteroalkyl, alkylaryl, alkylheteroaryl, alkylcycloalkyl, alkylcycloheteroalkyl alkyl sulfinyl, haloalkylsulfinyl, alkyl sulfonyl, haloalkylsulfonyl, alkylcarbonyl, haloalkylcarbonyl, alkoxycarbonyl, haloalkoxycarbonyl, alkyl aminocarbonyl, heteroalkylaminocarbonyl, di alkyl aminocarbonyl, and heterodialkylaminocarbonyl, each optionally substituted with one or more substituents individually chosen from $R^5$; and $R^5$ is chosen from hydroxy, halogen, —CN, —NO$_2$, amino, alkylamino, dialkylamino, alkyl, haloalkyl; alkylthio; haloalkylthio; alkoxy, haloalkoxy, alkenyl, haloalkenyl, alkynyl, haloalkynyl, aryl, heteroaryl, cycloalkyl, cycloheteroalkyl, alkylaryl, alkylheteroaryl, alkylcycloalkyl, alkylcycloheteroalkyl, alkyl sulfinyl, haloalkylsulfinyl, alkyl sulfonyl, haloalkylsulfonyl, alkylcarbonyl, haloalkylcarbonyl, alkoxycarbonyl, haloalkoxycarbonyl, alkyl aminocarbonyl, heteroalkylaminocarbonyl, di alkyl aminocarbonyl, and heterodialkylaminocarbonyl.

In certain embodiments of Formula II, $R^6$ can comprise an alkyl group, an aryl group, or an alkylaryl group. For example, $R^6$ can be a substituted or unsubstituted $C_1$-$C_8$ alkyl group. (e.g., a substituted or unsubstituted a $C_1$-$C_6$ alkyl group, or a substituted or unsubstituted a $C_1$-$C_4$ alkyl group).

In some embodiments, the compound can be defined by Formula III

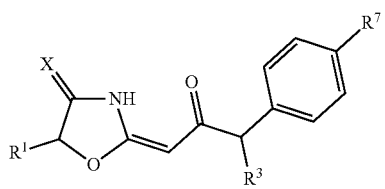

Formula III or a pharmaceutically acceptable salt or prodrug thereof, wherein $R^1$ is chosen from hydrogen, halogen, hydroxyl, —CN, —NO$_2$, amino, alkylamino, dialkylamino, alkyl, haloalkyl, alkylthio, haloalkylthio, alkoxy, haloalkoxy, alkenyl, haloalkenyl, alkynyl, haloalkynyl, aryl, heteroaryl, cycloalkyl, cycloheteroalkyl, alkylaryl, alkylheteroaryl, alkylcycloalkyl, alkyl cycloheteroalkyl, alkyl sulfinyl, haloalkylsulfinyl, alkyl sulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, dialkylaminocarbonyl, and heterodialkylaminocarbonyl, each optionally substituted with one or more substituents individually chosen from $R^5$; $R^3$ is chosen from hydrogen, halogen, hydroxyl, —CN, —NO$_2$, amino, alkylamino, dialkylamino, alkyl, haloalkyl, alkynyl, haloalkynyl, alkylthio, haloalkylthio, alkoxy, haloalkoxy, aryl, heteroaryl, cycloalkyl, cycloheteroalkyl, alkylaryl, alkylheteroaryl, alkylcycloalkyl, alkylcycloheteroalkyl alkyl sulfinyl, haloalkylsulfinyl, alkyl sulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, dialkylaminocarbonyl, and heterodialkylaminocarbonyl, each optionally substituted with one or more substituents individually chosen from $R^5$; $R^7$ is chosen from hydrogen, halogen, hydroxyl, —CN, —NO$_2$, amino, alkylamino, dialkylamino, alkyl, haloalkyl, alkenyl, haloalkenyl, alkynyl, haloalkynyl, alkylthio, haloalkylthio, alkoxy, haloalkoxy, aryl, heteroaryl, cycloalkyl, cycloheteroalkyl, alkylaryl, alkylheteroaryl, alkylcycloalkyl, alkylcycloheteroalkyl alkyl sulfinyl, haloalkylsulfinyl, alkyl sulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, di alkyl aminocarbonyl, and heterodialkylaminocarbonyl, each optionally substituted with one or more substituents individually chosen from $R^5$; and $R^5$ is chosen from hydroxy, halogen, —CN, —NO$_2$, amino, alkylamino, dialkylamino, alkyl, haloalkyl; alkylthio; haloalkylthio; alkoxy, haloalkoxy, alkenyl, haloalkenyl, alkynyl, haloalkynyl, aryl, heteroaryl, cycloalkyl, cycloheteroalkyl, alkylaryl, alkylheteroaryl, alkylcycloalkyl, alkylcycloheteroalkyl, alkyl sulfinyl, haloalkylsulfinyl, alkyl sulfonyl, haloalkylsulfonyl, alkylcarbonyl, haloalkylcarbonyl, alkoxy carbonyl, haloalkoxycarbonyl, alkylaminocarbonyl, heteroalkylaminocarbonyl, dialkylaminocarbonyl, and heterodialkylaminocarbonyl.

Also provided are compositions comprising one or more of the oxazolidinone derivatives described herein. For example, provided herein are pharmaceutical compositions that comprise a compound described herein in a pharmaceutically acceptable carrier. In some embodiments, pharmaceutical compositions can further include one or more additional active agents (e.g., one or more antibiotics, or one or more biofilm modulating agents).

Also provided are compositions that can prevent, remove, and/or inhibit biofilms. Biofilm preventing, removing, or inhibiting compositions can comprise a carrier and an effective amount of a compound described herein to prevent, remove, and/or inhibit a biofilm. The composition can be, for example, a dentifrice composition (e.g., a toothpaste, mouthwash, chewing gum, dental floss, or dental cream) that promotes dental hygiene by preventing, reducing, inhibiting or removing a biofilm.

The oxazolidinone derivatives described herein can exhibit anti-microbial activity and/or activity as biofilm modulating agents (e.g., activity as biofilm inhibitors and/or activity as biofilm dispersal agents). Accordingly, also provided are methods of treating subjects infected with a bacterium. Methods of treating a subject infected with a bacterium can comprise administering to the subject a therapeutically effective amount of a compound described herein. In some embodiments, the bacterium can comprise a Gram-positive bacterium. For example, the bacterium can include *Staphylococcus aureus* (methicillin sensitive), *Staphylococcus aureus* (methicillin resistant), *Staphylococcus aureus* (vancomycin resistant), *Streptococcus pneumonia* (penicillin sensitive), *Streptococcus pneumonia* (penicillin resistant), *Staphylococcus epidermis* (multiple drug resistant), *Enterococcus faecalis* (vancomycin sensitive), *Enterococcus faecium* (vancomycin resistant), and/or *Haemophilus influenzae*. In some embodiments, the bacterium can comprise a Gram-negative bacterium. For example, the bacterium can include *Salmonella, E. coli, Acinetobacter baumanii, Pseudomonas aeruginosa* or *Klebsiella pneumoniae*.

Also provided herein are methods for controlling biofilm formation on a substrate. Methods for controlling biofilm formation on a substrate can comprise contacting the substrate with a compound described herein in an amount effective to inhibit biofilm formation. The biofilm can comprise Gram-positive bacteria or Gram-negative bacteria. In some embodiments, the biofilm can comprise Gram-positive bacteria (e.g., a bacteria of a genus *Staphylococcus*, such as *Staphylococcus aureus*).

Also provided herein are methods for treating chronic bacterial infections. Methods for treating a chronic bacterial infection in a subject in need thereof can comprise administering to said subject a compound described herein in an amount effective to inhibit, reduce, or remove a biofilm component of the chronic bacterial infection. The chronic bacterial infection can comprise, for example, a urinary tract infection, gastritis, a respiratory infection, cystitis, pyelonephritis, osteomyelitis, bacteremia, a skin infection, rosacea, acne, a chronic wound infection, infectious kidney stones, bacterial endocarditis, or a sinus infection.

The compounds described herein can also be disposed on or within a substrate to control biofilm formation on the substrate. Accordingly, also provided are medical devices that comprise a medical device substrate and an effective amount of a compound described herein either coating the substrate, or incorporated into the substrate. The effective amount of the compound can be an effective amount to prevent or inhibit growth of a biofilm on the medical device substrate. The medical device substrate can include, for example, a stent, fastener, port, catheter, scaffold, and/or graft.

DETAILED DESCRIPTION

Definitions

Terms used herein will have their customary meaning in the art unless specified otherwise. The organic moieties mentioned when defining variable positions within the general formulae described herein (e.g., the term "halogen") are collective terms for the individual substituents encompassed by the organic moiety. The prefix $C_n$-$C_m$ indicates in each case the possible number of carbon atoms in the group.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

By "reduce" or other forms of the word, such as "reducing" or "reduction," is meant lowering of an event or characteristic (e.g., biofilm growth). It is understood that this is typically in relation to some standard or expected value, in other words it is relative, but that it is not always necessary for the standard or relative value to be referred to. For example, "reducing the biofilm component of a chronic bacterial infection" can refer to reducing the rate of growth of a biofilm component of the chronic bacterial infection relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

By "treat" or other forms of the word, such as "treated" or "treatment," is meant to administer a composition or to perform a method in order to reduce, prevent, inhibit, or eliminate a particular characteristic or event (e.g., a biofilm). The term "control" is used synonymously with the terms "treat" and "modulate."

"Biofilm" or "biofilms" refer to communities of microorganisms that are attached to a substrate. The microorganisms often excrete a protective and adhesive matrix of polymeric compounds. They often have structural heterogeneity, genetic diversity, and complex community interactions. "Biofilm preventing", "biofilm removing", "biofilm inhibiting", "biofilm reducing", "biofilm resistant", "biofilm controlling" or "antifouling" refer to prevention of biofilm formation, inhibition of the establishment or growth of a biofilm, or decrease in the amount of organisms that attach and/or grow upon a substrate, up to and including the complete removal of the biofilm.

As used herein, a "substrate" can include any living or nonliving structure. For example, biofilms often grow on synthetic materials submerged in an aqueous solution or exposed to humid air, but they also can form as floating mats on a liquid surface, in which case the microorganisms are adhering to each other or to the adhesive matrix characteristic of a biofilm.

An "effective amount" of a biofilm preventing, removing or inhibiting composition is that amount which is necessary to carry out the composition's function of preventing, removing or inhibiting a biofilm.

The term "alkyl," as used herein, refers to saturated straight, branched, cyclic, primary, secondary or tertiary hydrocarbons, including those having 1 to 20 atoms. In some embodiments, alkyl groups will include $C_1$-$C_{12}$, $C_1$-$C_{10}$, $C_1$-$C_8$, $C_1$-$C_5$, $C_1$-$C_4$, $C_1$-$C_3$, $C_1$-$C_2$, or $C_1$ alkyl groups. Examples of $C_1$-$C_{10}$ alkyl groups include, but are not limited to, methyl, ethyl, propyl, 1-methylethyl, butyl, 1-methylpropyl, 2-methylpropyl, 1,1-dimethyl ethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl groups, as well as their isomers. Examples of $C_1$-$C_4$-alkyl groups include, for example, methyl, ethyl, propyl, 1-methyl ethyl, butyl, 1-methylpropyl, 2-methylpropyl and 1,1-dimethylethyl groups.

Cyclic alkyl groups or "cycloalkyl" groups, which are encompassed alkyl, include cycloalkyl groups having from 3 to 10 carbon atoms. Cycloalkyl groups can include a single ring, or multiple condensed rings. In some embodiments, cycloalkyl groups include $C_3$-$C_4$, $C_4$-$C_7$, $C_5$-$C_7$, $C_4$-$C_6$, or $C_5$-$C_6$ cyclic alkyl groups. Non-limiting examples of cycloalkyl groups include adamantyl, cyclopropyl, cyclobutyl, cyclopentyl, cyclohexyl, cycloheptyl, cyclooctyl and the like.

Alkyl groups can be unsubstituted or substituted with one or more moieties selected from the group consisting of alkyl, halo, haloalkyl, hydroxyl, carboxyl, acyl, acyloxy, amino, alkyl- or dialkylamino, amido, arylamino, alkoxy, aryloxy, nitro, cyano, azido, thiol, imino, sulfonic acid, sulfate, sulfonyl, sulfanyl, sulfinyl, sulfamonyl, ester, phosphonyl, phosphinyl, phosphoryl, phosphine, thioester, thioether, acid halide, anhydride, oxime, hydrazine, carbamate, phosphoric acid, phosphate, phosphonate, or any other viable functional group that does not inhibit the biological activity of the compounds of the invention, either unprotected, or protected as necessary, as known to those skilled in the art, for example, as described in Greene, et al., *Protective Groups in Organic Synthesis*, John Wiley and Sons, Third Edition, 1999, hereby incorporated by reference.

Terms including the term "alkyl," such as "alkylcycloalkyl," "cycloalkylalkyl," "alkylamino," or "dialkylamino," will be understood to comprise an alkyl group as defined above linked to another functional group, where the group is linked to the compound through the last group listed, as understood by those of skill in the art.

The term "alkenyl," as used herein, refers to both straight and branched carbon chains which have at least one carbon-carbon double bond. In some embodiments, alkenyl groups can include $C_2$-$C_{20}$ alkenyl groups. In other embodiments, alkenyl can include $C_2$-$C_{12}$, $C_2$-$C_{10}$, $C_2$-$C_8$, $C_2$-$C_6$ or $C_2$-$C_4$ alkenyl groups. In one embodiment of alkenyl, the number of double bonds is 1-3, in another embodiment of alkenyl, the number of double bonds is one or two. Other ranges of carbon-carbon double bonds and carbon numbers are also contemplated depending on the location of the alkenyl moiety on the molecule. "$C_2$-$C_{10}$-alkenyl" groups may include more than one double bond in the chain. The one or more unsaturations within the alkenyl group may be located at any position(s) within the carbon chain as valence permits. In some embodiments, when the alkenyl group is covalently bound to one or more additional moieties, the carbon atom(s) in the alkenyl group that are covalently bound to the one or more additional moieties are not part of a carbon-carbon double bond within the alkenyl group. Examples of alkenyl groups include, but are not limited to, ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl groups.

The term "alkynyl," as used herein, refers to both straight and branched carbon chains which have at least one carbon-carbon triple bond. In one embodiment of alkynyl, the number of triple bonds is 1-3; in another embodiment of alkynyl, the number of triple bonds is one or two.

In some embodiments, alkynyl groups include from $C_2$-$C_{20}$ alkynyl groups. In other embodiments, alkynyl groups may include $C_2$-$C_{12}$, $C_2$-$C_{10}$, $C_2$-$C_8$, $C_2$-$C_6$ or $C_2$-$C_4$ alkynyl groups. Other ranges of carbon-carbon triple bonds and carbon numbers are also contemplated depending on the location of the alkenyl moiety on the molecule. For example, the term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl, and 4-methylpent-2-yn-5-yl groups.

The term "haloalkyl," as used herein refers to an alkyl group, as defined above, which is substituted by one or more halogen atoms. In some instances, the haloalkyl group can be an alkyl group substituted by one or more fluorine atoms. In certain instances, the haloalkyl group can be a perfluorinated alkyl group. For example $C_1$-$C_4$-haloalkyl includes, but is not limited to, chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, and pentafluoroethyl.

The term "haloalkenyl," as used herein, refers to an alkenyl group, as defined above, which is substituted by one or more halogen atoms.

The term "haloalkynyl," as used herein, refers to an alkynyl group, as defined above, which is substituted by one or more halogen atoms.

The term "alkoxy," as used herein, refers to alkyl-O—, wherein alkyl refers to an alkyl group, as defined above. Similarly, the terms "alkenyloxy," "alkynyloxy," "haloalkoxy," "haloalkenyloxy," "haloalkynyloxy," "cycloalkoxy," "cycloalkenyloxy," "halocycloalkoxy," and "halocycloalkenyloxy" refer to the groups alkenyl-O—, alkynyl-O—, haloalkyl-O—, haloalkenyl-O—, haloalkynyl-O—, cycloalkyl-O—, cycloalkenyl-O—, halocycloalkyl-O—, and halocycloalkenyl-O—, respectively, wherein alkenyl, alkynyl, haloalkyl, haloalkenyl, haloalkynyl, cycloalkyl, cycloalkenyl, halocycloalkyl, and halocycloalkenyl are as defined above. Examples of $C_1$-$C_6$-alkoxy include, but are not limited to, methoxy, ethoxy, $C_2H_5$—$CH_2O$—, $(CH_3)_2CHO$—, n-butoxy, $C_2H_5$—$CH(CH_3)O$—, $(CH_3)_2CH$—$CH_2O$—, $(CH_3)_3CO$—, n-pentoxy, 1-methylbutoxy, 2-methylbutoxy, 3-methylbutoxy, 1,1-dimethylpropoxy, 1,2-dimethylpropoxy, 2,2-dimethyl-propoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, and 1-ethyl-2-methylpropoxy.

The term "alkylthio," as used herein, refers to alkyl-S—, wherein alkyl refers to an alkyl group, as defined above. Similarly, the terms "haloalkylthio," "cycloalkylthio," and the like, refer to haloalkyl-S— and cycloalkyl-S— where haloalkyl and cycloalkyl are as defined above.

The term "alkylsulfinyl," as used herein, refers to alkyl-S(O)—, wherein alkyl refers to an alkyl group, as defined above. Similarly, the term "haloalkylsulfinyl" refers to haloalkyl-S(O)— where haloalkyl is as defined above.

The term "alkylsulfonyl," as used herein, refers to alkyl-S(O)$_2$—, wherein alkyl is as defined above. Similarly, the term "haloalkylsulfonyl" refers to haloalkyl-S(O)$_2$— where haloalkyl is as defined above.

The terms "alkylamino" and "dialkylamino," as used herein, refer to alkyl-NH— and (alkyl)$_2$N— groups, where alkyl is as defined above. Similarly, the terms "haloalkylamino" and "halodialkylamino" refer to haloalkyl-NH— and (haloalkyl)$_2$-NH—, where haloalkyl is as defined above.

The terms "alkylcarbonyl," "alkoxycarbonyl," "alkylaminocarbonyl," and "dialkylaminocarbonyl," as used herein, refer to alkyl-C(O)—, alkoxy-C(O)—, alkylamino-C(O)— and dialkylamino-C(O)— respectively, where alkyl, alkoxy, alkylamino, and dialkylamino are as defined above. Similarly, the terms "haloalkylcarbonyl," "haloalkoxycarbonyl," "haloalkylaminocarbonyl," and "dihaloalkylaminocarbonyl," as used herein, refer to the groups haloalkyl-C(O)—, haloalkoxy-C(O)—, haloalkylamino-C(O)—, and dihaloalkylamino-C(O)—, where haloalkyl, haloalkoxy, haloalkylamino, and dihaloalkylamino are as defined above.

The term "aryl," as used herein, refers to a monovalent aromatic carbocyclic group of from 6 to 14 carbon atoms. Aryl groups can include a single ring or multiple condensed rings. In some embodiments, aryl groups include $C_6$-$C_{10}$ aryl groups. Aryl groups include, but are not limited to, phenyl, biphenyl, naphthyl, tetrahydronaphtyl, phenylcyclopropyl and indanyl. Aryl groups may be unsubstituted or substituted by one or more moieties selected from halogen, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, cycloalkylthio, halocycloalkylthio, alkylsulfinyl, alkenylsulfinyl, alkynylsulfinyl, haloalkylsulfinyl, haloalkenylsulfinyl, haloalkynylsulfinyl, alkyl sulfonyl, alkenyl sulfonyl, alkynylsulfonyl, haloalkyl-sulfonyl, haloalkenylsulfonyl, haloalkynylsulfonyl, alkylamino, alkenylamino, alkynylamino, di(alkyl)amino, di(alkenyl)-amino, di(alkynyl) amino, or trialkylsilyl.

The term "alkylaryl," as used herein, refers to an aryl group that is bonded to a parent compound through a diradical alkylene bridge, (—$CH_2$-)$_n$, where n is 1-12 and where "aryl" is as defined above.

The term "alkylcycloalkyl," as used herein, refers to a cycloalkyl group that is bonded to a parent compound through a diradical alkylene bridge, (—$CH_2$-)$_n$, where n is 1-12 and where "cycloalkyl" is as defined above. The term "cycloalkylalkyl," as used herein, refers to a cycloalkyl group, as defined above, which is substituted by an alkyl group, as defined above.

The term "heteroalkyl," as used herein, refers to an alkyl group, as described above, which includes one or more heteroatoms (e.g., from one to four heteroatoms) within the carbon backbone. In some cases, the heteroatom(s) incorporated into the carbon backbone are oxygen, nitrogen, sulfur, or combinations thereof. The terms "heteroalkenyl" and "heteroalkynyl," as used herein, likewise refer to alkenyl and alkynyl groups respectively which include one or more heteroatoms (e.g., from one to four heteroatoms, such as oxygen, nitrogen, sulfur, or combinations thereof) within their carbon backbone.

The term "heteroaryl," as used herein, refers to a monovalent aromatic group of from 1 to 15 carbon atoms (e.g., from 1 to 10 carbon atoms, from 2 to 8 carbon atoms, from 3 to 6 carbon atoms, or from 4 to 6 carbon atoms) having one or more heteroatoms within the ring. The heteroaryl group can include from 1 to 4 heteroatoms, from 1 to 3 heteroatoms, or from 1 to 2 heteroatoms. In some cases, the heteroatom(s) incorporated into the ring are oxygen, nitrogen, sulfur, or combinations thereof. When present, the nitrogen and sulfur heteroatoms may optionally be oxidized. Heteroaryl groups can have a single ring (e.g., pyridyl or furyl) or multiple condensed rings provided that the point of attachment is through a heteroaryl ring atom.

Preferred heteroaryls include pyridyl, piridazinyl, pyrimidinyl, pyrazinyl, triazinyl, pyrrolyl, indolyl, quinolinyl, isoquinolinyl, quinazolinyl, quinoxalinnyl, furanyl, thiophenyl, furyl, pyrrolyl, imidazolyl, oxazolyl, isoxazolyl, isothiazolyl, pyrazolyl benzofuranyl, and benzothiophenyl. Heteroaryl rings may be unsubstituted or substituted by one or more moieties as described for aryl above.

The term "alkylheteroaryl," as used herein, refers to a heteroaryl group that is bonded to a parent compound through a diradical alkylene bridge, (—$CH_2$-)$_n$, where n is 1-12 and where "heteroaryl" is as defined above.

The terms "cycloheteroalkyl," "heterocyclyl," "heterocyclic," and "heterocyclo" are used herein interchangeably, and refer to fully saturated or unsaturated, cyclic groups, for example, 3 to 7 membered monocyclic or 4 to 7 membered monocyclic; 7 to 11 membered bicyclic, or 10 to 15 membered tricyclic ring systems, having one or more heteroatoms within the ring. The heterocyclyl group can include from 1 to 4 heteroatoms, from 1 to 3 heteroatoms, or from 1 to 2 heteroatoms. In some cases, the heteroatom(s) incorporated into the ring are oxygen, nitrogen, sulfur, or combinations thereof. When present, the nitrogen and sulfur heteroatoms may optionally be oxidized, and the nitrogen heteroatoms may optionally be quaternized. The heterocyclyl group may be attached at any heteroatom or carbon atom of the ring or ring system and may be unsubstituted or substituted by one or more moieties as described for aryl groups above.

Exemplary monocyclic heterocyclic groups include, but are not limited to, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

Exemplary bicyclic heterocyclic groups include, but are not limited to, indolyl, benzothiazolyl, benzoxazolyl, benzodioxolyl, benzothienyl, quinuclidinyl, quinolinyl, tetrahydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include carbazolyl, benzidolyl, phenanthrolinyl, acridinyl, phenanthridinyl, xanthenyl, and the like.

The term "alkylheterocyclyl" and "alkylcycloheteroalkyl" are used herein interchangeably, and refer to a heterocyclyl group that is bonded to a parent compound through a diradical alkylene bridge, (—CH$_2$-)$_n$, where n is 1-12 and where "heterocyclyl" is as defined above. The term "heterocyclylalkyl," as used herein, refers to a heterocyclyl group, as defined above, which is substituted by an alkyl group, as defined above.

The term "halogen," as used herein, refers to the atoms fluorine, chlorine, bromine and iodine. The prefix halo- (e.g., as illustrated by the term haloalkyl) refers to all degrees of halogen substitution, from a single substitution to a perhalo substitution (e.g., as illustrated with methyl as chloromethyl (—CH$_2$C$_1$), dichloromethyl (—CHCl$_2$), trichloromethyl (—CCl$_3$)).

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

Stereoisomers and polymorphic forms Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

The compounds described herein can exist and be isolated as optically active and racemic forms. The compounds can have one or more chiral centers, including at a sulfur atom, and thus exist as one or more stereoisomers. Where compounds include n chiral centers, the compounds can comprise up to $2^n$ optical isomers. Such stereoisomer-containing compounds can exist as a single enantiomer, a mixture of enantiomers, a mixture of diastereomers, or a racemic mixture. The optically active forms can be prepared by, for example, resolution of the racemic forms by selective crystallization techniques, by synthesis from optically active precursors, by chiral synthesis, by chromatographic separation using a chiral stationary phase or by enzymatic resolution.

The compounds can also be present in different solid forms, including different crystalline forms (i.e., different crystalline polymorphs of the compounds) or as an amorphous solid. In addition, the compounds can exist as hydrates or solvates, in which a certain stoichiometric amount of water or a solvent is associated with the molecule in the crystalline form. In some embodiments, the compositions described herein can include up to 15% (w/w), up to 20% (w/w), or up to 30% (w/w) of a particular solid form of the compounds described herein, based on the total weight of the composition.

Pharmaceutically Acceptable Salts

The compounds described herein can also be provided as pharmaceutically acceptable salts (e.g., acid or base salts) where applicable, of the compounds described herein. Pharmaceutically acceptable salts are known in the art. See, for example, Remington's Pharmaceutical Sciences, 20th ed., Lippincott Williams & Wilkins, Baltimore, Md., 2000, p. 704.

The term "acid salt" contemplates salts of the compounds with all pharmaceutically acceptable inorganic or organic acids. Inorganic acids include mineral acids such as hydrohalic acids such as hydrobromic acid and hydrochloric acid, sulfuric acid, phosphoric acids and nitric acid. Organic acids include all pharmaceutically acceptable aliphatic, alicyclic and aromatic carboxylic acids, dicarboxylic acids, tricarboxylic acids and fatty acids. In one embodiment of the acids, the acids are straight chain or branched, saturated or unsaturated C$_1$-C$_{20}$ aliphatic carboxylic acids, which are optionally substituted by halogen or by hydroxyl groups, or C$_6$-C$_{12}$ aromatic carboxylic acids. Examples of such acids are carbonic acid, formic acid, acetic acid, propionic acid, isopropionic acid, valeric acid, α-hydroxy acids such as glycolic acid and lactic acid, chloroacetic acid, benzoic acid, methane sulfonic acid, and salicylic acid. Examples of dicarboxylic acids include oxalic acid, malic acid, succinic acid, tartaric acid, fumaric acid, and maleic acid. An example of a tricarboxylic acid is citric acid. Fatty acids include all pharmaceutically acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glycoheptonic acid and lactobionic acid.

The term "base salt" contemplates salts of the compounds with all pharmaceutically acceptable inorganic or organic bases, including hydroxides, carbonates or bicarbonates of alkali metal or alkaline earth metals. Salts formed with such bases include, for example, the alkali metal and alkaline earth metal salts, including, but not limited to, as the lithium, sodium, potassium, magnesium or calcium salts. Salts formed with organic bases include the common hydrocarbon and heterocyclic amine salts, which include, for example, ammonium salts ($NH_4^+$), alkylammonium salts, and dialkylammonium salts, as well as salts of cyclic amines such as the morpholine and piperidine salts.

Prodrugs

The compounds described herein can also be provided as pharmaceutically acceptable prodrugs. Prodrugs of are compounds that, when metabolized in vivo, undergo conversion to compounds described herein having the desired pharmacological activity. Prodrugs can be prepared by replacing appropriate functionalities present in the compounds described herein with "pro-moieties" as described, for example, in H. Bundgaar, *Design of Prodrugs* (1985). Examples of prodrugs include ester, ether or amide derivatives of the compounds described herein, as well as their pharmaceutically acceptable salts. For further discussions of prodrugs, see, for example, T. Higuchi and V. Stella "Prodrugs as Novel Delivery Systems," ACS Symposium Series 14 (1975) and E. B. Roche ed., Bioreversible Carriers in Drug Design (1987).

Compounds

Provided herein are oxazolidinone derivatives that can exhibit anti-microbial activity and/or activity as biofilm modulating agents (e.g., activity as biofilm inhibitors and/or activity as biofilm dispersal agents). The compounds can exhibit potent activity anti-microbial activity (e.g., potent activity against Gram-positive positive bacteria including methicillin-resistant *Staphylococcus aureus*). The compounds can exhibit potent activity against biofilms. In some cases, the compounds can exhibit both anti-microbial activity and biofilm modulation properties.

For example, provided herein are compounds defined by Formula I

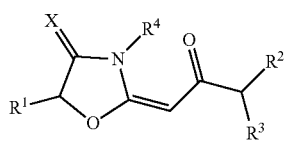

Formula I or a pharmaceutically acceptable salt or prodrug thereof, wherein X is chosen from O and S; $R^1$ is chosen from hydrogen, halogen, hydroxyl, —CN, —$NO_2$, amino, alkylamino, dialkylamino, alkyl, haloalkyl, alkylthio, haloalkylthio, alkoxy, haloalkoxy, alkenyl, haloalkenyl, alkynyl, haloalkynyl, aryl, heteroaryl, cycloalkyl, cycloheteroalkyl, alkylaryl, alkylheteroaryl, alkylcycloalkyl, alkylcycloheteroalkyl, alkylsulfinyl, haloalkylsulfinyl, alkyl sulfonyl, haloalkylsulfonyl, alkylcarbonyl, haloalkylcarbonyl, alkoxycarbonyl, haloalkoxycarbonyl, alkyl aminocarbonyl, heteroalkylaminocarbonyl, di alkyl aminocarbonyl, and heterodialkylaminocarbonyl, each optionally substituted with one or more substituents individually chosen from $R^5$; $R^2$ is chosen from alkylamino, dialkylamino, alkyl, haloalkyl, alkynyl, haloalkynyl, alkylthio, haloalkylthio, alkoxy, haloalkoxy, aryl, heteroaryl, cycloalkyl, cycloheteroalkyl, alkylaryl, alkylheteroaryl, alkylcycloalkyl, and alkylcycloheteroalkyl, each optionally substituted with one or more substituents individually chosen from $R^5$; $R^3$ is chosen from hydrogen, halogen, hydroxyl, —CN, —$NO_2$, amino, alkylamino, dialkylamino, alkyl, haloalkyl, alkynyl, haloalkynyl, alkylthio, haloalkylthio, alkoxy, haloalkoxy, aryl, heteroaryl, cycloalkyl, cycloheteroalkyl, alkylaryl, alkylheteroaryl, alkylcycloalkyl, alkylcycloheteroalkyl alkyl sulfinyl, haloalkylsulfinyl, alkyl sulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, dialkylaminocarbonyl, and heterodialkylaminocarbonyl, each optionally substituted with one or more substituents individually chosen from $R^5$; $R^4$ is chosen from hydrogen, alkyl, haloalkyl, alkylthio, haloalkylthio, alkenyl, haloalkenyl, alkynyl, haloalkynyl, aryl, heteroaryl, cycloalkyl, cycloheteroalkyl, alkylaryl, alkylheteroaryl, alkylcycloalkyl, and alkylcycloheteroalkyl, each optionally substituted with one or more substituents individually chosen from $R^5$; and $R^5$ is chosen from hydroxy, halogen, —CN, —$NO_2$, amino, alkylamino, di alkyl amino, alkyl, haloalkyl; alkylthio; haloalkylthio; alkoxy, haloalkoxy, alkenyl, haloalkenyl, alkynyl, haloalkynyl, aryl, heteroaryl, cycloalkyl, cycloheteroalkyl, alkylaryl, alkylheteroaryl, alkylcycloalkyl, alkylcycloheteroalkyl, alkyl sulfinyl, haloalkylsulfinyl, alkyl sulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, dialkylaminocarbonyl, and heterodialkylaminocarbonyl.

In some embodiments, X can be O. In other embodiments, X can be S.

In some embodiments, $R^1$ can comprise an alkyl group (e.g., a branched alkyl group). In some embodiments, $R^1$ can comprise a $C_1$-$C_4$ alkyl group (e.g., a $C_2$-$C_4$ alkyl group). In certain embodiments, $R^1$ can comprise a $C_3$-$C_4$ alkyl group (e.g., a branched $C_3$-$C_4$ alkyl group, such as an isopropyl group). In other embodiments, $R^1$ can comprise an aryl group or an alkylaryl group.

For example, $R^1$ can be a substituted or unsubstituted phenyl group or a substituted or unsubstituted benzyl group.

In some embodiments, $R^3$ can be hydrogen. In other embodiments, $R^3$ can comprise an alkyl group, an aryl group, or an alkylaryl group. For example, in some cases, $R^3$ is can be a substituted or unsubstituted aryl group (e.g., substituted or unsubstituted phenyl group or a substituted or unsubstituted benzyl group).

In some embodiments, $R^2$ can be hydrogen. In other embodiments, $R^2$ can comprise an alkyl group, an aryl group, or an alkylaryl group.

In some embodiments, $R^4$ is hydrogen. In other embodiments, $R^4$ can comprise an alkyl group, an aryl group, or an alkylaryl group. For example, $R^4$ can be a substituted or unsubstituted aryl group (e.g., substituted or unsubstituted phenyl group or a substituted or unsubstituted benzyl group) or a substituted or unsubstituted $C_1$-$C_4$ alkyl group.

In some embodiments, the compound can be defined by Formula II

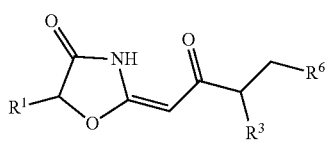

Formula II or a pharmaceutically acceptable salt or prodrug thereof, wherein $R^1$ is chosen from hydrogen, halogen, hydroxyl, —CN, —NO$_2$, amino, alkylamino, dialkylamino, alkyl, haloalkyl, alkylthio, haloalkylthio, alkoxy, haloalkoxy, alkenyl, haloalkenyl, alkynyl, haloalkynyl, aryl, heteroaryl, cycloalkyl, cycloheteroalkyl, alkylaryl, alkylheteroaryl, alkylcycloalkyl, alkylcycloheteroalkyl, alkyl sulfinyl, haloalkylsulfinyl, alkyl sulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, dialkylaminocarbonyl, and heterodialkylaminocarbonyl, each optionally substituted with one or more substituents individually chosen from $R^5$; $R^3$ is chosen from hydrogen, halogen, hydroxyl, —CN, —NO$_2$, amino, alkylamino, dialkylamino, alkyl, haloalkyl, alkynyl, haloalkynyl, alkylthio, haloalkylthio, alkoxy, haloalkoxy, aryl, heteroaryl, cycloalkyl, cycloheteroalkyl, alkylaryl, alkylheteroaryl, alkylcycloalkyl, alkylcycloheteroalkyl alkyl sulfinyl, haloalkylsulfinyl, alkyl sulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, dialkylaminocarbonyl, and heterodialkylaminocarbonyl, each optionally substituted with one or more substituents individually chosen from $R^5$; $R^6$ is chosen from hydrogen, halogen, hydroxyl, —CN, —NO$_2$, amino, alkylamino, dialkylamino, alkyl, haloalkyl, alkenyl, haloalkenyl, alkynyl, haloalkynyl, alkylthio, haloalkylthio, alkoxy, haloalkoxy, aryl, heteroaryl, cycloalkyl, cycloheteroalkyl, alkylaryl, alkylheteroaryl, alkylcycloalkyl, alkylcycloheteroalkyl alkyl sulfinyl, haloalkylsulfinyl, alkylsulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, di alkyl aminocarbonyl, and heterodialkylaminocarbonyl, each optionally substituted with one or more substituents individually chosen from $R^5$; and $R^5$ is chosen from hydroxy, halogen, —CN, —NO$_2$, amino, alkylamino, dialkylamino, alkyl, haloalkyl; alkylthio; haloalkylthio; alkoxy, haloalkoxy, alkenyl, haloalkenyl, alkynyl, haloalkynyl, aryl, heteroaryl, cycloalkyl, cycloheteroalkyl, alkylaryl, alkylheteroaryl, alkylcycloalkyl, alkylcycloheteroalkyl, alkyl sulfinyl, haloalkylsulfinyl, alkyl sulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, dialkylaminocarbonyl, and heterodialkylaminocarbonyl.

In certain embodiments of Formula II, $R^6$ can comprise an alkyl group, an aryl group, or an alkylaryl group. For example, $R^6$ can be a substituted or unsubstituted $C_1$-$C_8$ alkyl group. (e.g., a substituted or unsubstituted a $C_1$-$C_6$ alkyl group, or a substituted or unsubstituted a $C_1$-$C_4$ alkyl group).

In some embodiments, the compound can be defined by Formula III

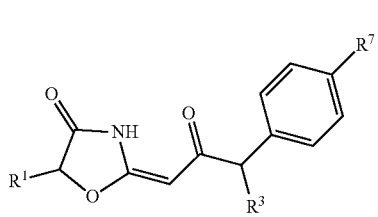

Formula III or a pharmaceutically acceptable salt or prodrug thereof, wherein $R^1$ is chosen from hydrogen, halogen, hydroxyl, —CN, —NO$_2$, amino, alkylamino, dialkylamino, alkyl, haloalkyl, alkylthio, haloalkylthio, alkoxy, haloalkoxy, alkenyl, haloalkenyl, alkynyl, haloalkynyl, aryl, heteroaryl, cycloalkyl, cycloheteroalkyl, alkylaryl, alkylheteroaryl, alkylcycloalkyl, alkyl cycloheteroalkyl, alkyl sulfinyl, haloalkylsulfinyl, alkyl sulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, dialkylaminocarbonyl, and heterodialkylaminocarbonyl, each optionally substituted with one or more substituents individually chosen from $R^5$; $R^3$ is chosen from hydrogen, halogen, hydroxyl, —CN, —NO$_2$, amino, alkylamino, dialkylamino, alkyl, haloalkyl, alkynyl, haloalkynyl, alkylthio, haloalkylthio, alkoxy, haloalkoxy, aryl, heteroaryl, cycloalkyl, cycloheteroalkyl, alkylaryl, alkylheteroaryl, alkylcycloalkyl, alkylcycloheteroalkyl alkyl sulfinyl, haloalkylsulfinyl, alkyl sulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, di alkyl aminocarbonyl, and heterodialkylaminocarbonyl, each optionally substituted with one or more substituents individually chosen from $R^5$; $R^7$ is chosen from hydrogen, halogen, hydroxyl, —CN, —NO$_2$, amino, alkylamino, dialkylamino, alkyl, haloalkyl, alkenyl, haloalkenyl, alkynyl, haloalkynyl, alkylthio, haloalkylthio, alkoxy, haloalkoxy, aryl, heteroaryl, cycloalkyl, cycloheteroalkyl, alkylaryl, alkylheteroaryl, alkylcycloalkyl, alkylcycloheteroalkyl alkyl sulfinyl, haloalkylsulfinyl, alkyl sulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, di alkyl aminocarbonyl, and heterodialkylaminocarbonyl, each optionally substituted with one or more substituents individually chosen from $R^5$; and $R^5$ is chosen from hydroxy, halogen, —CN, —NO$_2$, amino, alkylamino, dialkylamino, alkyl, haloalkyl; alkylthio; haloalkylthio; alkoxy, haloalkoxy, alkenyl, haloalkenyl, alkynyl, haloalkynyl, aryl, heteroaryl, cycloalkyl, cycloheteroalkyl, alkylaryl, alkylheteroaryl, alkylcycloalkyl, alkylcycloheteroalkyl, alkyl sulfinyl, haloalkylsulfinyl, alkyl sulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, dialkylaminocarbonyl, and heterodialkylaminocarbonyl.

In some embodiments, the compound can be defined by Formula IV

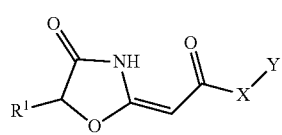

Formula IV or a pharmaceutically acceptable salt or prodrug thereof, wherein $R^1$ is chosen from hydrogen, halogen, hydroxyl, —CN, —NO₂, amino, alkylamino, dialkylamino, alkyl, haloalkyl, alkylthio, haloalkylthio, alkoxy, haloalkoxy, alkenyl, haloalkenyl, alkynyl, haloalkynyl, aryl, heteroaryl, cycloalkyl, cycloheteroalkyl, alkylaryl, alkylheteroaryl, alkylcycloalkyl, alkyl cycloheteroalkyl, alkyl sulfinyl, haloalkylsulfinyl, alkyl sulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, dialkylaminocarbonyl, and heterodialkylaminocarbonyl, each optionally substituted with one or more substituents individually chosen from $R^5$; X is absent or, represents a bivalent linking moiety; Y is chosen from —NH₂, —NR⁹R¹⁰, —NR⁹R¹⁰, or —⁺NR⁹R¹⁰R¹¹, $R^9$, $R^{10}$, and $R^{11}$ are individually chosen from alkyl, haloalkyl, alkenyl, haloalkenyl, alkynyl, haloalkynyl, alkylthio, haloalkylthio, alkoxy, haloalkoxy, aryl, heteroaryl, cycloalkyl, cycloheteroalkyl, alkylaryl, alkylheteroaryl, alkylcycloalkyl, alkylcycloheteroalkyl alkylsulfinyl, haloalkylsulfinyl, alkyl sulfonyl, haloalkylsulfonyl, alkylcarbonyl, haloalkylcarbonyl, alkoxycarbonyl, haloalkoxycarbonyl, alkyl aminocarbonyl, heteroalkylaminocarbonyl, dialkylaminocarbonyl, and heterodialkylaminocarbonyl, each optionally substituted with one or more substituents individually chosen from $R^5$; and $R^5$ is chosen from hydroxy, halogen, —CN, —NO₂, amino, alkylamino, dialkylamino, alkyl, haloalkyl; alkylthio; haloalkylthio; alkoxy, haloalkoxy, alkenyl, haloalkenyl, alkynyl, haloalkynyl, aryl, heteroaryl, cycloalkyl, cycloheteroalkyl, alkylaryl, alkylheteroaryl, alkylcycloalkyl, alkylcycloheteroalkyl, alkylsulfinyl, haloalkylsulfinyl, alkyl sulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, dialkylaminocarbonyl, and heterodialkylaminocarbonyl.

In some embodiments, $R^1$ can comprise an alkyl group (e.g., a branched alkyl group). In some embodiments, $R^1$ can comprise a $C_1$-$C_4$ alkyl group (e.g., a $C_2$-$C_4$ alkyl group). In certain embodiments, $R^1$ can comprise a $C_3$-$C_4$ alkyl group (e.g., a branched $C_3$-$C_4$ alkyl group, such as an isopropyl group). In other embodiments, $R^1$ can comprise an aryl group or an alkylaryl group. For example, $R^1$ can be a substituted or unsubstituted phenyl group or a substituted or unsubstituted benzyl group.

In some embodiments, X is absent. On other embodiments, X is present. When present, the linking group can be any suitable group or moiety which is at minimum bivalent, and connects Y to the carbonyl moiety. The linking group can be composed of any assembly of atoms. In some cases, the total number of atoms in the linking group can be from 3 to 20 atoms (e.g., from 3 to 15 atoms, or from 3 to 10 atoms). In some embodiments, the linking group can be, for example, an alkyl, alkoxy, alkylaryl, alkylheteroaryl, alkylcycloalkyl, alkylheterocycloalkyl, alkylthio, alkylsulfinyl, alkylsulfonyl, alkylamino, dialkylamino, alkyl carbonyl, alkoxycarbonyl, alkylaminocarbonyl, dialkylaminocarbonyl, or polyamino group.

In some embodiments, $R^9$, $R^{10}$, and $R^{11}$, when present, represent alkyl groups (e.g., linear alkyl groups or branched alkyl group). In some embodiments, $R^9$, $R^{10}$, and $R^{11}$, when present, can comprise a $C_1$-$C_4$ alkyl group (e.g., a $C_2$-$C_4$ alkyl group). In certain embodiments, $R^9$, $R^{10}$ and $R^{11}$, when present, can comprise a $C_3$-$C_4$ alkyl group (e.g., a branched $C_3$-$C_4$ alkyl group, such as an isopropyl group). In other embodiments, $R^9$, $R^{10}$, and $R^{11}$, when present, can comprise an aryl group or an alkylaryl group In some embodiments, the compound can be defined by Formula V

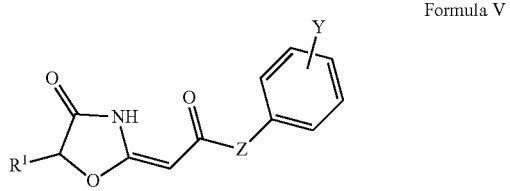

Formula V or a pharmaceutically acceptable salt or prodrug thereof, wherein $R^1$ is chosen from hydrogen, halogen, hydroxyl, —CN, —NO₂, amino, alkylamino, dialkylamino, alkyl, haloalkyl, alkylthio, haloalkylthio, alkoxy, haloalkoxy, alkenyl, haloalkenyl, alkynyl, haloalkynyl, aryl, heteroaryl, cycloalkyl, cycloheteroalkyl, alkylaryl, alkylheteroaryl, alkylcycloalkyl, alkyl cycloheteroalkyl, alkyl sulfinyl, haloalkylsulfinyl, alkyl sulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, dialkylaminocarbonyl, and heterodialkylaminocarbonyl, each optionally substituted with one or more substituents individually chosen from $R^5$; Z is absent or represents a bivalent linking moiety; Y is chosen from —NH₂, —NR⁹R¹⁰, or —⁺NR⁹R¹⁰R¹¹; $R^9$, $R^{10}$, and $R^{11}$ are individually chosen from alkyl, haloalkyl, alkenyl, haloalkenyl, alkynyl, haloalkynyl, alkylthio, haloalkylthio, alkoxy, haloalkoxy, aryl, heteroaryl, cycloalkyl, cycloheteroalkyl, alkylaryl, alkylheteroaryl, alkylcycloalkyl, alkylcycloheteroalkyl alkylsulfinyl, haloalkylsulfinyl, alkylsulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, dialkylaminocarbonyl, and heterodialkylaminocarbonyl, each optionally substituted with one or more substituents individually chosen from $R^5$; and $R^5$ is chosen from hydroxy, halogen, —CN, —NO₂, amino, alkylamino, dialkylamino, alkyl, haloalkyl; alkylthio; haloalkylthio; alkoxy, haloalkoxy, alkenyl, haloalkenyl, alkynyl, haloalkynyl, aryl, heteroaryl, cycloalkyl, cycloheteroalkyl, alkylaryl, alkylheteroaryl, alkylcycloalkyl, alkylcycloheteroalkyl, alkylsulfinyl, haloalkylsulfinyl, alkylsulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, dialkylaminocarbonyl, and heterodialkylaminocarbonyl.

In some embodiments, $R^1$ can comprise an alkyl group (e.g., a branched alkyl group). In some embodiments, $R^1$ can comprise a $C_1$-$C_4$ alkyl group (e.g., a $C_2$-$C_4$ alkyl group). In certain embodiments, $R^1$ can comprise a $C_3$-$C_4$ alkyl group (e.g., a branched $C_3$-$C_4$ alkyl group, such as an isopropyl group). In other embodiments, $R^1$ can comprise an aryl group or an alkylaryl group. For example, $R^1$ can be a substituted or unsubstituted phenyl group or a substituted or unsubstituted benzyl group.

In some embodiments, Z is absent. On other embodiments, Z is present. When present, the linking group can be any suitable group or moiety which is at minimum bivalent, and connects the carbonyl moiety and the substituted phenyl group. The linking group can be composed of any assembly of atoms. In some cases, the total number of atoms in the linking group can be from 3 to 20 atoms (e.g., from 3 to 15 atoms, or from 3 to 10 atoms). In some embodiments, the linking group can be, for example, an alkyl, alkoxy, alkylaryl, alkylheteroaryl, alkylcycloalkyl, alkylheterocycloalkyl, alkylthio, alkylsulfinyl, alkylsulfonyl, alkylamino, dialkylamino, alkylcarbonyl, alkoxycarbonyl, alkylaminocarbonyl, di alkyl aminocarbonyl, or polyamino group.

In some embodiments, $R^9$, $R^{10}$, and $R^{11}$, when present, represent alkyl groups (e.g., linear alkyl groups or branched alkyl group). In some embodiments, $R^9$, $R^{10}$, and $R^{11}$, when present, can comprise a $C_1$-$C_4$ alkyl group (e.g., a $C_2$-$C_4$ alkyl group). In certain embodiments, $R^9$, $R^{10}$, and $R^{11}$, when present, can comprise a $C_3$-$C_4$ alkyl group (e.g., a branched $C_3$-$C_4$ alkyl group, such as an isopropyl group). In other embodiments, $R^9$, $R^{10}$, and $R^{11}$, when present, can comprise an aryl group or an alkylaryl group Compositions Also provided are compositions that include one or more of the compounds described herein. In some embodiments, anti-microbial compositions and/or biofilm preventing, removing or inhibiting compositions are provided, comprising a carrier and an effective amount of a compound described herein.

In some embodiments, the carrier can be a pharmaceutically acceptable carrier. A "pharmaceutically acceptable carrier" as used herein refers to a carrier that, when combined with a compound described herein, facilitates the application or administration of that compound described herein for its intended purpose (e.g., to exhibit anti-microbial activity and/or to prevent or inhibit biofilm formation, or remove an existing biofilm). The compound described herein may be formulated for administration in a pharmaceutically acceptable carrier in accordance with known techniques. See, e.g., Remington, The Science and Practice of Pharmacy (9th Ed. 1995). The pharmaceutically acceptable carrier can, of course, also be acceptable in the sense of being compatible with any other ingredients in the composition.

The carrier may be a solid or a liquid, or both, and is preferably formulated with the a compound described herein as a unit-dose composition, for example, a tablet, which may contain from 0.01 or 0.5% to 95% or 99% by weight of the a compound described herein. One or more a compounds described herein can be included in the compositions, which may be prepared by any of the well-known techniques of pharmacy comprising admixing the components, optionally including one or more accessory ingredients.

In general, compositions may be prepared by uniformly and intimately admixing a compound described herein with a liquid or finely divided solid carrier, or both, and then, if necessary, shaping the resulting mixture. For example, a tablet may be prepared by compressing or molding a powder or granules containing the a compound described herein, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Compositions can be formulated to be suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) or transdermal administration, although the most suitable route in any given case will depend on the nature and severity of the condition being treated and on the nature of the particular compound that is being used.

Compositions suitable for oral administration may be presented in discrete units, such as capsules, cachets, lozenges, or tablets, each containing a predetermined amount of the compound; as a powder or granules; as a solution or a suspension in an aqueous or non-aqueous liquid; or as an oil-in-water or water-in-oil emulsion. Such compositions may be prepared by any suitable method of pharmacy, which includes the step of bringing into association the compound and a suitable carrier (which may contain one or more accessory ingredients as noted above).

Compositions suitable for buccal (sub-lingual) administration include lozenges comprising the compound in a flavored base, usually sucrose and acacia or tragacanth; and pastilles comprising the compound in an inert base such as gelatin and glycerin or sucrose and acacia.

Compositions suitable for parenteral administration comprise sterile aqueous and non-aqueous injection solutions of the compound, which preparations are preferably isotonic with the blood of the intended recipient. These preparations may contain anti-oxidants, buffers, bacteriostats and solutes that render the composition isotonic with the blood of the intended recipient. Aqueous and non-aqueous sterile suspensions may include suspending agents and thickening agents. The compositions may be presented in unit/dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described.

For example, the composition can be an injectable, stable, sterile composition comprising a compound described herein in a unit dosage form in a sealed container. The composition can be provided in the form of a lyophilizate that can be reconstituted with a suitable pharmaceutically acceptable carrier to form a liquid composition suitable for injection thereof into a subject. The unit dosage form can comprise from about 10 mg to about 10 grams of the compound. When the compound or salt is substantially water-insoluble, a sufficient amount of emulsifying agent that is physiologically acceptable may be employed in sufficient quantity to emulsify the compound or salt in an aqueous carrier. One such useful emulsifying agent is phosphatidyl choline.

Compositions suitable for rectal administration can be presented as unit dose suppositories. These may be prepared by mixing the active compound with one or more conventional solid carriers, for example, cocoa butter, and then shaping the resulting mixture.

Compositions suitable for topical application to the skin can take the form of an ointment, cream, lotion, paste, gel, spray, aerosol, or oil. Carriers that may be used include petroleum jelly, lanoline, polyethylene glycols, alcohols, transdermal enhancers, and combinations of two or more thereof.

Compositions suitable for transdermal administration can be presented as discrete patches adapted to remain in intimate contact with the epidermis of the recipient for a prolonged period of time. Compositions suitable for transdermal administration may also be delivered by iontophoresis and typically take the form of an optionally buffered aqueous solution of the active compound.

In some embodiments, the compositions described herein can further include one or more additional active agents, such as a biocide. A "biocide" as used herein refers to a substance with the ability to kill or to inhibit the growth of microorganisms (e.g., bacteria, fungal cells, protozoa, etc.), which is not compound described in the compounds section above. Common biocides include oxidizing and non-oxidizing chemicals.

In some embodiments, the compositions described herein can further include one or more antibiotics. An "antibiotic" as used herein is a type of "biocide." Common antibiotics include aminoglycosides, carbacephems (e.g., loracarbef), carbapenems, cephalosporins, glycopeptides (e.g., teicoplanin and vancomycin), macrolides, monobactams (e.g., aztreonam) penicillins, polypeptides (e.g., bacitracin, colistin, polymyxin B), quinolones, sulfonamides, tetracyclines, etc. Antibiotics treat infections by either killing or preventing the growth of microorganisms. Many act to inhibit cell wall synthesis or other vital protein synthesis of the microorganisms.

Aminoglycosides are commonly used to treat infections caused by Gram-negative bacteria such as *Escherichia coli* and *Klebsiella*, particularly *Pseudomonas aeroginosa*. Examples of aminoglycosides include, but are not limited to amikacin, gentamicin, kanamycin, neomycin, netilmicin, streptomycin, tobramycin, and paromomycin.

Carbapenems are broad-specrum antibiotics, and include, but are not limited to, ertapenem, doripenem, imipenem/cilstatin, and meropenem.

Cephalosporins include, but are not limited to, cefadroxil, cefazolin, cefalotin (cefalothin), cefalexin, cefaclor, cefamandole, cefoxitin, cefprozil, loracarbef, cefuroxime, cefixime, cefdinir, cefditoren, cefoperazone, cefotaxime, cefpodoxime, ceftazidime, ceftibuten, ceftizoxime, ceftriaxone, cefepime, cefpirome, and ceftobiprole.

Macrolides include, but are not limited to, azithromycin, clarithromycin, dirithromycin, erythromycin, roxithromycin, troleandomycin, telithromycin and spectinomycin.

Penicillins include, but are not limited to, amoxicillin, ampicillin, azlocillin, bacampicillin, carbenicillin, cloxacillin, dicloxacillin, flucloxacillin, mezlocillin, meticillin, nafcillin, oxacillin, penicillin, piperacillin and ticarcillin.

Quinolones include, but are not limited to, ciprofloxacin, enoxacin, gatifloxacin, gemifloxacin, levofloxacin, lomefloxacin, moxifloxacin, norfloxacin, ofloxacin and trovafloxacin.

Sulfonamides include, but are not limited to, mafenide, prontosil, sulfacetamide, sulfamethizole, sulfanilamide, sulfasalazine, sulfisoxazole, trimethoprim, and co-trimoxazole (trimethoprim-sulfamethoxazole).

Tetracyclines include, but are not limited to, demeclocycline, doxycycline, minocycline, oxytetracycline and tetracycline.

Other antibiotics include arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin (rifampicin), tinidazole, etc.

In some embodiments, the composition can be a dentifrice composition comprising one or more of the compounds described herein. A "dentifrice" is a substance that is used to clean the teeth. It may be in the form of, e.g., a paste or powder. Commonly known dentifrices include toothpaste, mouthwash, chewing gum, dental floss, and dental cream. Other examples of dentifrices include toothpowder, mouth detergent, troches, dental or gingival massage cream, dental strips, dental gels, and gargle tablets. Examples of dentifrice compositions comprising toothpaste and mouthwash are found in U.S. Pat. No. 6,861,048 (Yu et al.); U.S. Pat. No. 6,231,836 (Takhtalian et al.); and U.S. Pat. No. 6,331,291 (Glace et al.); each of which are incorporated by reference herein in their entirety.

Coating compositions are also provided. A "coating" as used herein is generally known. Any of a variety of organic and aqueous coating compositions, with or without pigments, may be modified to contain one or more compounds described herein. Examples of suitable coating compositions include, for example, the coating compositions described in U.S. Pat. Nos. 7,109,262, 6,964,989, 6,835,459, 6,677,035, 6,528,580, and 6,235,812, each incorporated by reference herein in their entirety.

In some examples, coating compositions can comprise (in addition to one or more compounds described herein) a film-forming resin, an aqueous or organic solvent that disperses the resin; and, optionally, at least one pigment. Other ingredients such as colorants, secondary pigments, stabilizers and the like can be included if desired. The one or more biofilm modulating compounds described herein may be dissolved or dispersed in the solvent and/or resin, so that the compound(s) are dispersed or distributed on the substrate an article coated by the coating composition. The resin may comprise, for example, a polymeric material. A polymeric material is a material that is comprised of large molecules made from associated smaller repeating structural units, often covalently linked. Common examples of polymeric materials are unsaturated polyester resins, and epoxy resins.

Any suitable article can be coated, in whole or in part, with the coating compositions described herein. Suitable articles include, but are not limited to, automobiles and airplanes (including substrates such as wing and propeller surfaces for aerodynamic testing), vessel hulls (including interior and exterior surfaces thereof), pressure vessels (including interior and exterior surfaces thereof), medical devices (e.g., implants), windmills, etc. Coating of the article with the composition can be carried out by any suitable means, such as by brushing, spraying, electrostatic deposition, dip coating, doctor blading, etc.

Devices

Also provided are medical devices that comprise a medical device substrate and an effective amount of a compound described herein either coating the substrate, or incorporated into the substrate. The effective amount of the compound can be an effective amount to prevent or inhibit growth of a biofilm on the medical device substrate.

"Medical device" as used herein refers to an object that is inserted or implanted in a subject or applied to a surface of a subject. Common examples of medical devices include stents, fasteners, ports, catheters, scaffolds and grafts. A "medical device substrate" can be made of a variety of biocompatible materials, including, but not limited to, metals, ceramics, polymers, gels, and fluids not normally found within the human body. Examples of polymers useful in fabricating medical devices include such polymers as silicones, rubbers, latex, plastics, polyanhydrides, polyesters, polyorthoesters, polyamides, polyacrylonitrile, polyurethanes, polyethylene, polytetrafluoroethylene, polyethylenetetraphthalate, etc. Medical devices can also be fabricated using naturally-occurring materials or treated with naturally-occurring materials. Medical devices can include any combination of artificial materials, e.g., combinations selected because of the particular characteristics of the components. Medical devices can be intended for short-term or long-term residence where they are positioned. A hip implant is intended for several decades of use, for example. By contrast, a tissue expander may only be needed for a few months, and is removed thereafter.

Some examples of medical devices are found in U.S. Pat. No. 7,081,133 (Chinn et al.); U.S. Pat. No. 6,562,295 (Neuberger); and U.S. Pat. No. 6,387,363 (Gruskin); each incorporated by reference herein in their entirety.

Methods of Use

The oxazolidinone derivatives described herein can exhibit anti-microbial activity and/or activity as biofilm modulating agents (e.g., activity as biofilm inhibitors and/or activity as biofilm dispersal agents). Accordingly, also provided are methods of treating subjects infected with a bacterium. Methods of treating a subject infected with a bacterium can comprise administering to the subject a therapeutically effective amount of a compound described herein.

The bacterium can comprise Gram-positive bacteria or Gram-negative bacteria. In some embodiments, the bacterium can comprise Gram-positive bacteria. Examples of Gram-positive bacteria affected by the oxazolidinone derivatives described herein include, but are not limited to, bacteria of the genera *Listeria, Staphylococcus, Streptococcus, Bacillus, Corynebacterium, Peptostreptococcus,* and *Clostridium*. For example, the bacterium can include *Listeria monocytogenes, Staphylococcus aureus, Streptococcus pyogenes, Streptococcus pneumoniae, Bacillus cereus, Bacillus anthracis, Clostridium botulinum, Clostridium perfringens, Clostridium difficile, Clostridium tetani, Corynebacterium diphtheriae, Corynebacteruim ulcerans,* and *Peptostreptococcus anaerobius*. Other examples of Gram-positive bacteria include, for example, bacteria of the genera *Actinomyces, Propionibacterium, Nocardia* and *Streptomyces*. In certain embodiments, the bacterium can include *Staphylococcus aureus* (methicillin sensitive), *Staphylococcus aureus* (methicillin resistant), *Staphylococcus aureus* (vancomycin resistant), *Streptococcus pneumonia* (penicillin sensitive), *Streptococcus pneumonia* (penicillin resistant), *Staphylococcus epidermis* (multiple drug resistant), *Enterococcus faecalis* (vancomycin sensitive), *Enterococcus faecium* (vancomycin resistant), and/or *Haemophilus influenzae*.

In some embodiments, the bacterium can comprise Gram-negative bacteria. Examples of Gram-negative bacteria affected by the oxazolidinone derivatives described herein include, but are not limited to, bacteria of the genera *Escherichia, Salmonella, Vibrio, Helicobacter, Pseudomonas, Bordetella, Vibrio, Haemophilus, Halomonas,* and *Acinetobacter*. For example, the bacteria can include *Pseudomonas aeuroginosa, Bordetella pertussis, Vibrio vulnificus, Haemophilus influenzae, Halomonas pacifica,* and *Acinetobacter baumannii*. Other examples of Gram-negative bacteria include, for example, bacteria of the genera *Klebsiella, Proteus, Neisseria, Helicobacter, Brucella, Legionella, Campylobacter, Francisella, Pasteurella, Yersinia, Bartonella, Bacteroides, Streptobacillus, Spirillum, Moraxella* and *Shigella*. In some embodiments, the bacterium can comprise a Gram-negative bacterium. For example, the bacterium can include *Salmonella, E. Coli, Acinetobacter baumanii, Pseudomonas aeruginosa* or *Klebsiella pneumoniae*.

The oxazolidinone derivatives described herein can also exhibit activity as biofilm modulating agents. Accordingly, methods of controlling biofilm formation on a substrate are disclosed, comprising the step of administering a compound described herein to a substrate in an amount effective to inhibit biofilm formation.

A "substrate" as used herein is a base on which an organism, such as those commonly found in biofilms, may live. The term "substrate," as used herein, refers to any substrate, whether in an industrial or a medical setting, that provides or can provide an interface between an object and a fluid, permitting at least intermittent contact between the object and the fluid. A substrate, as understood herein, further provides a plane whose mechanical structure, without further treatment, is compatible with the adherence of microorganisms. Substrates compatible with biofilm formation may be natural or synthetic, and may be smooth or irregular. Fluids contacting the substrates can be stagnant or flowing, and can flow intermittently or continuously, with laminar or turbulent or mixed flows. A substrate upon which a biofilm forms can be dry at times with sporadic fluid contact, or can have any degree of fluid exposure including total immersion. Fluid contact with the substrate can take place via aerosols or other means for air-borne fluid transmission.

Biofilm formation with health implications can involve those substrates in all health-related environments, including substrates found in medical environments and those substrates in industrial or residential environments that are involved in those functions essential to human well being, for example, nutrition, sanitation and the prevention of disease. Substrates found in medical environments include the inner and outer aspects of various instruments and devices, whether disposable or intended for repeated uses. Examples include the entire spectrum of articles adapted for medical use, including scalpels, needles, scissors and other devices used in invasive surgical, therapeutic or diagnostic procedures; implantable medical devices, including artificial blood vessels, catheters and other devices for the removal or delivery of fluids to patients, artificial hearts, artificial kidneys, orthopedic pins, plates and implants; catheters and other tubes (including urological and biliary tubes, endotracheal tubes, peripherably insertable central venous catheters, dialysis catheters, long term tunneled central venous catheters, peripheral venous catheters, short term central venous catheters, arterial catheters, pulmonary catheters, Swan-Ganz catheters, urinary catheters, peritoneal catheters), urinary devices (including long term urinary devices, tissue bonding urinary devices, artificial urinary sphincters, urinary dilators), shunts (including ventricular or arterio-venous shunts); prostheses (including breast implants, penile prostheses, vascular grafting prostheses, heart valves, artificial joints, artificial larynxes, otological implants), vascular catheter ports, wound drain tubes, hydrocephalus shunts, pacemakers and implantable defibrillators, and the like. Other examples will be readily apparent to practitioners in these arts. Substrates found in the medical environment also include the inner and outer aspects of pieces of medical equipment, medical gear worn or carried by personnel in the health care setting. Such substrates can include counter tops and fixtures in areas used for medical procedures or for preparing medical apparatus, tubes and canisters used in respiratory treatments, including the administration of oxygen, of solubilized drugs in nebulizers and of anesthetic agents. Also included are those substrates intended as biological barriers to infectious organisms in medical settings, such as gloves, aprons and faceshields. Commonly used materials for biological barriers may be latex-based or non-latex based. Vinyl is commonly used as a material for non-latex surgical gloves. Other such substrates can include handles and cables for medical or dental equipment not intended to be sterile. Additionally, such substrates can include those non-sterile external substrates of tubes and other apparatus found in areas where blood or body fluids or other hazardous biomaterials are commonly encountered.

Substrates in contact with liquids are particularly prone to biofilm formation. As an example, those reservoirs and tubes used for delivering humidified oxygen to patients can bear biofilms inhabited by infectious agents. Dental unit waterlines similarly can bear biofilms on their substrates, providing a reservoir for continuing contamination of the system of flowing an aerosolized water used in dentistry. Sprays, aerosols and nebulizers are highly effective in disseminating biofilm fragments to a potential host or to another environmental site. It is especially important to health to prevent biofilm formation on those substrates from where biofilm fragments can be carried away by sprays, aerosols or nebulizers contacting the substrate.

Other substrates related to health include the inner and outer aspects of those articles involved in water purification, water storage and water delivery, and articles involved in food processing. Substrates related to health can also include the inner and outer aspects of those household articles involved in providing for nutrition, sanitation or disease prevention. Examples can include food processing equipment for home use, materials for infant care, tampons and toilet bowls. "Substrate" as used herein also refers to a living substrate, such as the inner ear of a patent.

Substrates can be smooth or porous, soft or hard. Substrates can include a drainpipe, glaze ceramic, porcelain, glass, metal, wood, chrome, plastic, vinyl, Formica® brand laminate, or any other material that may regularly come in contact with an aqueous solution in which biofilms may form and grow. The substrate can be a substrate commonly found on household items such as shower curtains or liners, upholstery, laundry, and carpeting.

A substrate on which biofilm preventing, removing or inhibiting is important is that of a ship hull. Biofilms, such as those of *Halomonas pacifica*, promote the corrosion of the hull of ships and also increase the roughness of the hull, increasing the drag on the ship and thereby increasing fuel costs. The biofilm can also promote the attachment of larger living structures such as barnacles on the ship hull. Fuel can account for half of the cost of marine shipping, and the loss in fuel efficiency due to biofilm formation is substantial.

Substrates on which biofilms can adhere include those of living organisms, as in the case of humans with chronic infections caused by biofilms, as discussed above. Biofilms can also form on the substrates of food contact surfaces, such as those used for processing seafood, and also on food products themselves. Examples of seafood products that may have biofilm contamination include oysters. Human infections caused by the ingestion of raw oysters has been linked to *Vibrio vulnificus* bacterium. *Vibrio* bacteria attach to algae and plankton in the water and transfer to the oysters and fish that feed on these organisms.

Other examples of substrates or devices on which biofilms can adhere can be found in U.S. Pat. Nos. 5,814,668 and 7,087,661; and U.S. Pat. Application Publication Nos. 2006/0228384 and 2006/0018945, each of which is incorporated herein by reference in its entirety.

In some embodiments, methods of enhancing the effects of a biocide are disclosed, comprising the step of administering a compound described herein in combination with a biocide, the active compound being administered in an amount effective to enhance the effects of the biocide.

"Administering" or "administration of" a compound described herein and/or biocide as used herein in inclusive of contacting, applying, etc. (e.g., contacting with an aqueous solution, contacting with a surface (e.g., a hospital surface such as a table, instrumentation, etc.)), in addition to providing to a subject (for example, to a human subject in need of treatment for a microbial infection).

"Enhancing" the effects of a biocide by administering a compound described herein in combination with the biocide refers to increasing the effectiveness of the biocide, such that the microorganism killing and/or growth inhibition is higher at a certain concentration of the biocide administered in combination with the active compound than without. In some embodiments, a bacteria or other microorganism is "sensitized" to the effects of a biocide, such that the bacteria or other microorganism that was resistant to the biocide prior to administering the compound described herein (e.g., little to none, or less than 20, 10, 5 or 1% are killed upon application) is rendered vulnerable to that biocide upon or after administering the compound (e.g., greater than 20, 30, 40, 50, 60, 70, 80, 90, or 95% or more are killed).

As used herein, the administration of two or more compounds (inclusive of the compounds described herein and biocides) "in combination" means that the two compounds are administered closely enough in time that the administration of or presence of one alters the biological effects of the other. The two compounds may be administered simultaneously (concurrently) or sequentially.

Simultaneous administration of the compounds may be carried out by mixing the compounds prior to administration, or by administering the compounds at the same point in time but at different anatomic sites or using different routes of administration, or administered at times sufficiently close that the results observed are indistinguishable from those achieved when the compounds are administered at the same point in time.

Sequential administration of the compounds may be carried out by administering, e.g., an active compound at some point in time prior to administration of a biocide, such that the prior administration of active compound enhances the effects of the biocide (e.g., percentage of microorganisms killed and/or slowing the growth of microorganisms). In some embodiments, an active compound is administered at some point in time prior to the initial administration of a biocide. Alternatively, the biocide may be administered at some point in time prior to the administration of an active compound, and optionally, administered again at some point in time after the administration of an active compound.

Also provided herein are methods for controlling biofilm formation on a substrate. Methods for controlling biofilm formation on a substrate can comprise contacting the substrate with a compound described herein in an amount effective to inhibit biofilm formation.

The biofilm can comprise Gram-positive bacteria or Gram-negative bacteria. In some embodiments, the biofilm can comprise Gram-positive bacteria. Examples of Gram-positive bacteria affected by compounds described herein include, but are not limited to, bacteria of the genera *Listeria, Staphylococcus, Streptococcus, Bacillus, Corynebacterium, Peptostreptococcus*, and *Clostridium*. For example, the bacteria can include *Listeria monocytogenes, Staphylococcus aureus, Streptococcus pyogenes, Streptococcus pneumoniae, Bacillus cereus, Bacillus anthracis, Clostridium botulinum, Clostridium perfringens, Clostridium difficile, Clostridium tetani, Corynebacterium diphtheritic, Corynebacteruim ulcerans*, and *Peptostreptococcus anaerobius*. Other examples of Gram-positive bacteria include, for example, bacteria of the genera *Actinomyces, Propionibacterium, Nocardia* and *Streptomyces*.

In some embodiments, the biofilm can comprise Gram-negative bacteria. Examples of Gram-positive bacteria affected by compounds described herein include, but are not limited to, bacteria of the genera *Escherichia, Salmonella, Vibrio, Helicobacter, Pseudomonas, Bordetella, Vibrio, Haemophilus, Halomonas,* and *Acinetobacter*. For example, the bacteria can include *Pseudomonas aeuroginosa, Bordetella pertussis, Vibrio vulnificus, Haemophilus influenzae, Halomonas pacifica,* and *Acinetobacter baumannii*. Other examples of Gram-negative bacteria include, for example, bacteria of the genera *Klebsiella, Proteus, Neisseria, Helicobacter, Brucella, Legionella, Campylobacter, Francisella, Pasteurella, Yersinia, Bartonella, Bacteroides, Streptobacillus, Spirillum, Moraxella* and *Shigella*.

Also provided are methods for treating chronic bacterial infections in a subject in need thereof. These methods can comprise administering a compound described herein to a subject in an amount effective to inhibit, reduce, or remove a biofilm component of said chronic bacterial infection. "Treating" as used herein refers to any type of activity that imparts a benefit to a patient afflicted with a disease, including improvement in the condition of the patient (e.g., in one or more symptoms), delay in the progression of the disease, delay in onset of the disease, etc.

A "chronic bacterial infection" is a bacterial infection that is of a long duration or frequent recurrence. For example, a chronic middle ear infection, or otitis media, can occur when the Eustachian tube becomes blocked repeatedly due to allergies, multiple infections, ear trauma, or swelling of the adenoids. The definition of "long duration" will depend upon the particular infection. For example, in the case of a chronic middle ear infection, it may last for weeks to months. Other known chronic bacterial infections include urinary tract infection (most commonly caused by *Escherichia coli* and/or *Staphylococcus saprophyticus*), gastritis (most commonly caused by *Helicobacter pylori*), respiratory infection (such as those commonly afflicting patents with cystic fibrosis, most commonly caused by *Pseudomonas aeuroginosa*), cystitis (most commonly caused by *Escherichia coli*), pyelonephritis (most commonly caused by *Proteus species, Escherichia coli* and/or *Pseudomonas* species), osteomyelitis (most commonly caused by *Staphylococcus aureus*, but also by *Escherichia coli*), bacteremia, skin infection, rosacea, acne, chronic wound infection, infectious kidney stones (can be caused by *Proteus mirabilis*), bacterial endocarditis, and sinus infection. A common infection afflicting pigs is atrophic rhinitis (caused by *Bordatella* species, e.g. *Bordatella rhinitis*).

Also disclosed is a method of clearing a preformed biofilm from a substrate comprising the step of administering an effective amount of a compound described herein to said substrate, wherein said effective amount will reduce the amount of said biofilm on said substrate.

"Preformed biofilm" is a biofilm that has begun to adhere to a substrate. The biofilm may or may not yet be fully formed.

By way of non-limiting illustration, examples of certain embodiments of the present disclosure are given below.

EXAMPLES

Materials and Methods

THF and dichloromethane were purified using an alumina filtration system. Aldehydes were purchased from a commercial chemical company and used as received. Reactions were monitored by TLC analysis (pre-coated silica gel 60 F254 plates, 250 mm layer thickness) and visualization was accomplished with a 254 nm UV light and by staining with a KMnO4 solution (1.5 g of KMnO$_4$, 10 g of K2CO3, and 1.25 mL of a 10% NaOH solution in 200 mL of water). Reactions were also monitored by LC-MS (2.6 mm C18 50×2.10 mm column). Flash chromatography on SiO$_2$ was used to purify the crude reaction mixtures and performed on a flash system utilizing pre-packed cartridges and linear gradients.

Melting points were determined using a capillary melting point apparatus. Infrared spectra were determined on a FT/IR spectrometer. $^1$H, $^{13}$C and NMR spectra were obtained on a 400 MHz instrument in CDCl$_3$ unless otherwise noted. Chemical shifts were reported in parts per million with the residual solvent peak used as an internal standard (CDCl$_3$=7.26 ppm for $^1$H and 77.16 ppm for $^{13}$C). $^1$H NMR spectra were run at 300 or 400 MHz and are tabulated as follows: chemical shift, multiplicity (s=singlet, d=doublet, t=triplet, q=quartet, p=pentet, m=multiplet, bs=broad singlet, dt=doublet of triplet, tt=triplet of triplet), number of protons, and coupling constant(s). $^{13}$C NMR spectra were run at 100 MHz or 175 MHz using a proton-decoupled pulse sequence with a dl of 0 second unless otherwise noted, and are tabulated by observed peak. High-resolution mass spectra were obtained on an ion trap mass spectrometer using heated electrospray ionization (HESI).

General Procedure for the Preparation of O-TBS-α-Hydroxy Amides from α-Amino Acids The amino acid (10 mmol) was dissolved in 1 M H$_2$SO$_4$ (10 mmol) and cooled to 0° C. Then 2 M NaNO$_2$ (20 mmol) was added dropwise and the reaction was allowed to slowly warm to room temperature and stirred overnight. Then another aliquot of 2 M NaNO$_2$ (10 mmol) was added and the reaction was stirred for a further 24 hours at room temperature. The reaction mixture was then extracted with ethyl acetate (7×10 mL). The combined organic layers were washed with brine (15 mL), dried (MgSO$_4$), filtered and concentrated. The resulting crude white solid was dissolved in DMF (2 M). Then imidazole (42 mmol) and TBSCl (21 mmol) were added and the reaction was stirred for 24 hours at room temperature. The reaction was then diluted with EtOAc and washed with 10% citric acid, sat. NaHCO$_3$, water and brine. The organic layer was then dried (MgSO$_4$), filtered and concentrated, leaving an oil. Then p-toluenesulfonyl chloride (10 mmol), silica supported ammonium chloride (20 mmol) (reference) and Et$_3$N (80 mmol) were added to the crude oil. The reaction was stirred for 10 minutes at room temperature and then diluted with EtOAc, filtered and concentrated. The residue was purified by column chromatography on SiO$_2$ (20% EtOAc:Hex).

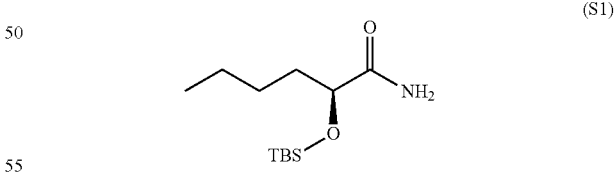

(S1)

(S)-2-((tert-Butyldimethylsilyl)oxy)hexanamide (S1). Yield: 240 mg (54%) of S1 as a colorless oil that solidified upon standing: R$_f$=0.15 (4:1 hexanes:EtOAc); [α]$_D$=−24° (c=7.9, dichloromethane); $^1$H NMR (400 MHz, CDCl$_3$); δ=7.04 (bs, 1H), 6.47 (bs, 1H), 4.05 (t, J=7.5 Hz, 1H), 1.68-1.59 (m, 2H), 1.32-1.23 (m, 4H), 0.85-0.80 (m, 12H), 0.02 (s, 6H); $^{13}$C NMR (100 MHz, CDCl$_3$): δ=178.2, 73.6, 35.1, 26.6, 26.0, 22.9, 18.3, 14.3, −4.6, −5.0. IR (film) 3483, 3287, 3197, 2954, 2860, 1688, 1469; HRMS (ESI) m/z calculated for C$_{12}$H$_{27}$NO$_2$Si [M+H]$^+$: 246.1884, found: 246.1878.

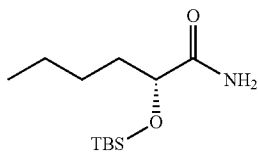
(S2)

(R)-2-((tert-Butyldimethylsilyl)oxy)hexanamide (S2). Yield: 90 mg (53%) of S2 as a colorless oil that solidified upon standing: $R_f$=0.15 (4:1 hexanes:EtOAc); $[\alpha]_D$=+23.5° (c=2.1, dichloromethane); $^1$H NMR (400 MHz, CDCl$_3$); δ=6.52 (bs, 1H), 6.30 (bs, 1H), 4.11 (t, J=7.5 Hz, 1H), 1.75-1.65 (m, 2H), 1.38-1.26 (m, 4H), 0.91-0.85 (m, 12H), 0.07 (s, 6H); $^{13}$C NMR (100 MHz, CDCl$_3$); δ=177.8, 73.8, 35.3, 26.7, 26.2, 23.0, 18.4, 14.4, −4.4, −4.8. IR (film) 3483, 3287, 3197, 2954, 2860, 1688, 1469; HRMS (ESI) m/z calculated for C$_{12}$H$_{27}$NO$_2$Si [M+H]$^+$: 246.1884, found: 246.1877.

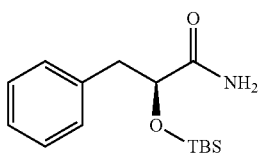
(S3)

(S)-2-((tert-butyldimethylsilyl)oxy)-3-phenylpropanamide (S3). Yield: 190 mg (32%) of S3 as a white solid. $R_f$=0.20 (hexanes/EtOAc=1:1); $^1$H NMR (400 MHz, CDCl$_3$): δ=7.30-7.16 (m, 5H), 6.68-6.63 (s, 1H), 6.48-6.42 (s, 1H), 4.28-4.23 (dd, J=7.7, 2.6 Hz, 1H), 3.14-3.06 (dd, J=13.6, 2.9 Hz, 1H), 2.88-2.80 (dd, J=13.6, 8.1 Hz, 1H), 0.90 (s, 9H), −0.08 (s, 3H), −0.28 (s, 3H); $^{13}$C NMR (100 MHz, CDCl$_3$): δ=177.2, 137.5, 130.3, 128.4, 126.9, 75.0, 42.0, 26.0, 18.2, −5.3, −5.4; IR (film) 3480. 3283, 3261, 2942, 2889, 1682, 1162; HRMS (ESI) m/z calculated for C$_{15}$H$_{25}$NO$_2$Si [M+H]$^+$: 280.17278, found: 280.17278.

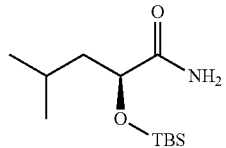
(S4)

(S)-2-((tert-butyldimethylsilyl)oxy)-4-methylpentanamide (S4). Yield: 187 mg (36%) of S4 as a white solid. $R_f$=0.18 (hexanes/EtOAc=4:1); $^1$H NMR (400 MHz, CDCl$_3$): δ=7.05 (s, 1H), 6.46 (s, 1H), 4.06-4.03 (dd, J=7.3, 4.4 Hz, 1H), 1.80-1.70 (m, 1H), 1.60-1.44 (m, 2H), 0.90-0.85 (m, 15H), 0.06 (s, 3H), 0.04 (s, 3H); $^{13}$C NMR (100 MHz, CDCl$_3$): δ=178.4, 72.5, 44.9, 25.9, 24.2, 23.6, 22.5, 18.2, −4.7, −5.0.

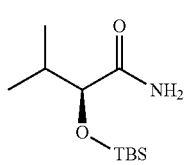
(S5)

(S)-2-((tert-butyldimethylsilyl)oxy)-3-methylbutanamide (S5). Yield: 280 mg (30%) of S5 as a white solid. $R_f$=0.18 (hexanes/EtOAc=4:1); $^1$H NMR (400 MHz, CDCl$_3$): δ=7.15 (s, 1H), 6.30 (s, 1H), 3.86-3.83 (d, J=3.3 Hz, 1H), 2.03-1.95 (m, 1H), 0.91-0.87 (d, J=7.0 Hz, 3H), 0.85 (s, 9H), 0.83-0.79 (d, J=7.0 Hz, 3H), 0.03 (s, 3H), 0.01 (s, 3H); $^{13}$C NMR (100 MHz, CDCl$_3$): δ=177.5, 77.9, 32.7, 25.9, 19.4, 18.2, 16.4, −4.9, −5.0; IR (film) 3471, 3205, 3142, 2954, 2926, 1658, 1461; HRMS (ESI) m/z calculated for C$_{11}$H$_{25}$NO$_2$Si [M+H]$^+$: 232.17273, found: 232.17273.

(S6)

(2S,3S)-2-((tert-butyldimethylsilyl)oxy)-3-methylpentanamide (S6). Yield: 160 mg (34%) of S6 as a white solid. $R_f$=0.18 (hexanes/EtOAc=4:1); $^1$H NMR (400 MHz, CDCl$_3$): δ=6.62 (s, 1H), 6.48 (s, 1H), 3.99-3.95 (d, J=3.7 Hz, 1H), 1.81-1.70 (m, 1H), 1.55-1.43 (m, 1H), 1.27-1.14 (m, 1H), 0.96-0.84 (m, 15H), 0.09 (s, 3H), 0.06 (s, 3H); $^{13}$C NMR (100 MHz, CDCl$_3$): δ=177.1, 69.6, 39.9, 26.0, 23.9, 18.2, 15.6, 12.2, −4.7, −4.9; IR (film) 3484, 3278, 2959, 2927, 1685, 1464; FIRMS (ESI) m/z calculated for C$_{12}$H$_{27}$NO$_2$Si [M+H]$^+$: 246.18838, found: 246.18831.

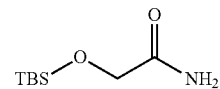
(S7)

2-((tert-Butyldimethylsilyl)oxy)acetamide (S7). 2-hydroxy acetamide (250 mg, 3.3 mmol) was dissolved in DMF (2.5 mL) and imidazole (340 mg, 4.9 mmol) and TBSCl (560 mg, 3.6 mmol) were added at room temperature. The resulting mixture was stirred for 24 h. The reaction was diluted with ethyl acetate (20 mL) and washed with 10% citric acid (15 mL), sat. aq. NaHCO$_3$ (15 mL), water (15 mL) and brine (15 mL). The organic layer was dried (MgSO$_4$), filtered and concentrated in vacuo. The residue was purified by chromatography on SiO$_2$ (3:1 hexanes:EtOAc) to yield 530 mg (85%) of S7 as an oily solid: $R_f$=0.25 (3:1 hexanes:EtOAc); $^1$H NMR (400 MHz, CDCl$_3$); δ=6.83 (bs, 1H), 6.59 (bs, 1H), 4.03 (s, 2H), 0.88 (s, 9H), 0.07 (s, 6H); $^{13}$C NMR (100 MHz, CDCl$_3$): δ=175.3, 63.3, 26.1, 18.5, −5.3; IR (film) 3471, 3275, 3157, 2950, 2856, 1688, 1113; HRMS (ESI) m/z calculated for C$_8$H$_{19}$NO$_2$Si [M+H]$^+$: 190.1258, found: 190.1255.

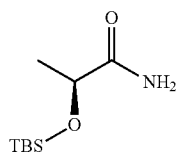

(S)-2-((tert-Butyldimethylsilyl)oxy)propanamide (S8). (S)-lactamide (1.0 g, 11 mmol) was dissolved in dichloromethane (20 mL) and cooled to 0° C. and triethyl amine (2.3 mL, 17 mmol) and DMAP (130 mg, 1.1 mmol) were added followed by TBSCl (1.9 g, 12 mmol) as a solution in dichloromethane (6 mL). The reaction was slowly warmed to room temperature and stirred for 24 h, diluted with water (10 mL) and extracted with dichloromethane (3×10 mL). The combined organic layers were washed with 10% citric acid (10 mL), saturated NaHCO$_3$ (10 mL), water (10 mL) and brine (10 mL), dried (MgSO$_4$), filtered and concentrated in vacuo. The residue was purified by chromatography on SiO$_2$ (3:1 hexanes:EtOAc) to yield 2.0 g (89%) of S8 as an oil: R$_f$=0.25 (3:1 hexanes:EtOAc); [α]$_D$=−7.5° (c=10, dichloromethane); $^1$H NMR (400 MHz, CDCl$_3$); δ=6.60 (bs, 1H), 5.64 (bs, 1H), 4.21 (q, J=7.0 Hz, 1H), 1.38 (d, J=6.8 Hz, 3H), 0.92 (s, 9H), 0.11 (s, 6H); $^{13}$C NMR (100 MHz, CDCl$_3$); δ=179.7, 70.4, 33.9, 27.0, 22.5, 14.0; IR (film) 3480, 3282, 3195, 2955, 2931, 2860, 1693, 1121; HRMS (ESI) m/z calculated for C$_9$H$_{21}$NO$_2$Si [M+H]$^+$: 204.1414, found: 204.1411.

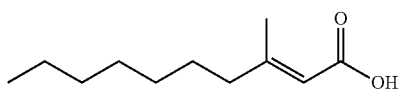

(E)-3-Methyldec-2-enoic acid (S9). 1-iodoheptane (4.5 mL, 27 mmol) was dissolved in pentane (81 mL) and diethyl ether (54 mL) and cooled to −78° C. followed by addition of tBuLi (1.7 M solution in pentane, 33 mL, 56 mmol) and the reaction was allowed to stir at −78° C. for 5 minutes, the dry ice/acetone bath was removed and the reaction was warmed to room temperature and stirred for 1.5 h. The resulting heptyl Li solution was cooled to 0° C. and was added to a solution of CuI (2.55 g, 13.4 mmol) in THF (13.5 mL) at 0° C. The reaction was stirred for 10 minutes and then cooled to −78° C. at which point a solution of 2-butynoic acid (0.50 g, 5.8 mmol) in THF (12 mL) was added and the reaction was stirred at −78° C. for 10 minutes and then warmed to −5° C. and stirred for 45 minutes. The reaction was poured into cooled (0° C.) 1 M HCl (100 mL) and extracted with EtOAc (3×30 mL), the combined organic layers were washed with brine (20 mL), dried (MgSO$_4$), filtered, concentrated and purified by chromatography on SiO$_2$ (10% EtOAc:hexanes) to yield 860 mg (81%) of S9 as a colorless oil: $^1$H NMR (400 MHz, CDCl$_3$); δ=11.49 (bs, 1H), 5.68 (s, 1H), 2.17-2.13 (m, 5H), 1.51-1.27 (m, 10H), 0.88 (t, J=6.7 Hz, 3H); $^{13}$C NMR (100 MHz, CDCl$_3$); δ=172.9, 163.8, 115.3, 41.5, 32.0, 29.4, 29.3, 27.6, 22.9, 19.3, 14.3.

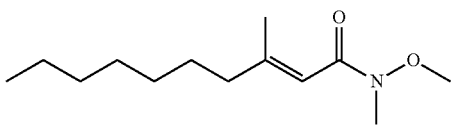

(E)-N-methoxy-N,3-dimethyldec-2-enamide (S10). (E)-3-methyldec-2-enoic acid (120 mg, 0.66 mmol) was dissolved in THF (2.1 mL) and 2-chloro-4,6-dimethoxy-1,3,5-triazine (140 mg, 0.79 mmol) was added followed by the addition of N-methylmorpholine (0.22 mL, 2.0 mmol). The reaction was stirred at room temperature for 1 h and N,O-dimethylhydroxylamine hydrochloride (66 mg, 0.66 mmol) was added and the reaction was stirred at room temperature overnight. Water (10 mL) was added and the reaction was extracted with Et$_2$O (2×10 mL). The combined organic layers were washed with sat. aq. NaHCO$_3$ (5 mL), 1 M HCl (5 mL), brine (5 mL), dried (MgSO$_4$), filtered and concentrated to yield 150 mg (99%) of S10 as an oil (90% purity): R$_f$=0.33 (20% EtOAc:hexanes); $^1$H NMR (400 MHz, CDCl$_3$); δ=5.99 (s, 1H), 3.55 (s, 3H), 3.07 (s, 3H), 2.04-1.99 (m, 5H), 1.38-1.34 (m, 2H), 1.22-1.11 (m, 8H), 0.76 (t, J=7.1 Hz, 3H); $^{13}$C NMR (100 MHz, CDCl$_3$); δ=173.9, 156.7, 113.6, 61.2, 55.7, 40.1, 31.7, 29.0, 28.9, 27.4, 22.5, 18.4, 13.9; IR (film) 2955, 2931, 2856, 1657, 1638 1461, 1366; HRMS (ESI) m/z calculated for C$_{13}$H$_{25}$NO$_2$ [M+H]$^+$: 228.19581, found: 228.19579.

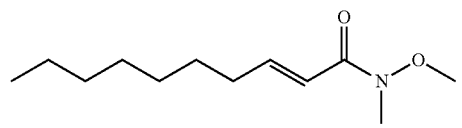

(E)-N-Methoxy-N-methyldec-2-enamide (S11). Trans-2-decenoic acid (500 mg, 2.8 mmol) was dissolved in THF (8 mL) and 2-chloro-4,6-dimethoxy-1,3,5-triazine (610 mg, 3.4 mmol) was added followed by the addition of N-methylmorpholine (0.93 mL, 8.4 mmol). The reaction was stirred at room temperature for 1 h, N,O-dimethylhydroxylamine hydrochloride (280 mg, 2.8 mmol) was added and the reaction was stirred at room temperature overnight. Water (15 mL) was added and the reaction was extracted with Et$_2$O (2×10 mL), combined organic layers were washed with saturated NaHCO$_3$ (10 mL), 1 M HCl (10 mL), brine (10 mL), dried (MgSO$_4$), filtered and concentrated to yield 590 mg (99%) of S11 as an oil: R$_f$=0.23 (20% EtOAc:hexanes); $^1$H NMR (400 MHz, CDCl$_3$); δ=6.97 (dt, J=15.8, 6.9 Hz, 1H), 6.38 (d, J=15.1 Hz, 1H), 3.69 (s, 3H), 3.23 (s, 3H), 2.22 (q, J=7.2 Hz, 2H), 1.46 (m, 2H), 1.32-1.21 (m, 8H), 0.87 (t, J=6.9 Hz, 3H); $^{13}$C NMR (100 MHz, CDCl$_3$); δ=167.3, 148.3, 118.8, 61.8, 32.7, 32.6, 32.0, 29.4, 29.3, 28.5, 22.8, 14.2.

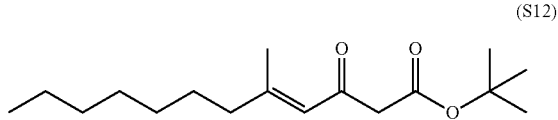 [SMILES: CCCCCCC/C(C)=C/C(=O)CC(=O)OC(C)(C)C]

tert-Butyl (E)-5-methyl-3-oxodec-4-enoate (S12). Tert-butyl acetate (0.23 mL, 1.7 mmol) was added to freshly prepared solution of LDA (0.17 mL, 1.2 mmol diisopropyl amine; 0.71 mL, 1.2 mmol, 1.7 M nBuLi; 0.6 mL THF) at −78° C. and stirred for 15 minutes. Then (E)-N-methoxy-N,3-dimethyldec-2-enamide (130 mg, 0.57 mmol) was added as a solution in THF (0.6 mL). The reaction was stirred at −78° C. for 2 h. It was then removed from the dry ice/acetone bath and after 5 minutes at room temperature sat. aq. NaHCO$_3$ (5 mL) was added. Then the reaction was extracted with EtOAc (2×10 mL) and the combined organic layers were washed with saturated NH$_4$Cl (10 mL), dried (MgSO$_4$), filtered, concentrated in vacuo and purified by chromatography on SiO$_2$ (10% EtOAc:hexanes) to yield 89 mg (55%) of S12 as an oil: R$_f$=0.15 (10% EtOAc:hexanes); $^1$H NMR (400 MHz, CDCl$_3$); δ=6.08 (s, 1H), 3.34 (s, 2H), 2.13 (m, 5H), 1.45 (s, 9H), 1.26 (m, 10H), 0.87 (t, J=7.1 Hz, 3H); $^{13}$C NMR (100 MHz, CDCl$_3$): δ=192.7, 167.2, 161.9, 122.1, 81.6, 52.3, 41.5, 31.9, 29.3, 29.2, 28.1, 27.6, 22.8, 19.8, 14.2; IR (film) 3007, 2957, 2927, 2855, 1734, 1685, 1620, 1249, 1144; HRMS (ESI) m/z calculated for C$_{17}$H$_{30}$O$_3$ [M+Na]$^+$: 305.20872, found: 305.20827.

(S13)

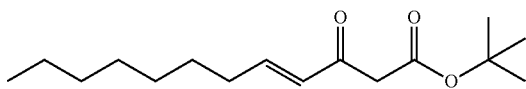

tert-Butyl (E)-3-oxododec-4-enoate (S13). Tert-butyl acetate (1.1 mL, 8.2 mmol) was added to freshly prepared LDA (1.2 mL, 8.5 mmol diisopropyl amine; 4.7 mL, 8.4 mmol, 1.80 M nBuLi; 4.2 mL THF) at −78° C. and stirred for 15 minutes. Then (E)-N-methoxy-N-methyldec-2-enamide (580 mg, 2.7 mmol) was added as a solution in THF (2.7 mL). The reaction was stirred at −78° C. for 2 h, removed from the dry ice/acetone bath and after 5 minutes at room temperature sat. aq. NaHCO$_3$ (5 mL) was added. Then the reaction was extracted with EtOAc (2×10 mL) and the combined organic layers were washed with saturated NH$_4$Cl (10 mL), dried (MgSO$_4$), filtered, concentrated in vacuo and purified by chromatography on SiO$_2$ (5% EtOAc:hexanes) to yield 330 mg (42%) of S13 as an oil: R$_f$=0.30 (5% EtOAc:hexanes); Enol and keto forms are reported as observed with major tautomer integrated to 1: $^1$H NMR (400 MHz, CDCl$_3$); δ=6.85 (dt, 0.1=15.8, 6.9 Hz, 0.6H), 6.58 (d, 0.1=15.8, 6.9 Hz, 1H), 6.10 (d, 0.1=15.1 Hz, 0.6H), 5.74 (d, J=15.1 Hz, 1H), 4.86 (s, 1H), 3.46 (s, 1H), 2.24-2.12 (m, 4H), 1.47-1.25 (m, 38H), 0.85 (t, J=6.9 Hz, 6H); $^{13}$C NMR (100 MHz, CDCl$_3$): δ=192.5, 172.7, 168.8, 166.5, 149.5, 140.2, 129.5, 124.2, 91.3, 81.5, 80.5, 48.1, 32.4, 31.6, 31.5, 29.0, 28.9, 28.8, 28.4, 28.1, 27.8, 27.7, 22.4, 22.3, 13.9; IR (film) 3004, 2977, 2958, 2926, 1735, 1665, 1253, 1144; FIRMS (ESI) m/z calculated for C$_{16}$H$_{28}$O$_3$ [M+Na]$^+$: 291.19307, found: 291.19283.

General Procedure for Synthesis of 4-Oxazolidinones:

Procedure A for the synthesis of 4-oxazolidinones containing an α,β unsaturated ketone. Tert-butyl-β-keto ester (0.32 mmol) was dissolved in acetone (0.12 M) and cooled to −78° C. and trifluoroacetic anhydride (0.6 M), trifluoroacetic acid (0.18 M) and acetic anhydride (0.74 M) were added. The reaction was allowed to slowly warm to room temperature and was stirred overnight. The reaction was then poured into sat. aq. NaHCO$_3$ (10 mL), extracted with EtOAc (2×10 mL), organic layers were washed with brine (5 mL), dried (MgSO$_4$), filtered, and concentrated in vacuo. The residue was loaded onto a plug of SiO$_2$ and eluted with 20% EtOAc:hexanes (100 mL). The crude dioxanone and O-TBS-α-hydroxy amide (0.08 mmol) were dissolved in p-xylene (0.8 mL) and stirred at reflux for 1 h. The reaction was cooled to room temperature and concentrated in vacuo. The residue was loaded onto a plug of SiO$_2$ and eluted with 10% EtOAc:hexanes (100 mL). The resulting crude imide was dissolved in dichloromethane (0.8 mL) and trifluoroacetic acid (0.8 mL) was added at room temperature. The reaction was allowed to stir for 24 h, concentrated in vacuo and purified by chromatography on SiO$_2$ (20% EtOAc:hexanes).

Procedure B for the synthesis of 4-oxazolidinones containing a saturated ketone. Acylated Meldrum's acid derivatives were synthesized following a previously reported procedure. In brief, the Carboxylic acid (1 mmol) was dissolved in dichloromethane (0.5 M) and then N,N'-dicylcohexylcarbodiimide (1.1 mmol) and 4-dimethylaminopyridine (0.1 mmol) were added. Then Meldrum's acid (1 mmol) was added and the reaction is stirred at room temperature overnight. The insoluble urea is filtered and the solvent is removed in vacuo and redissolved in EtOAc and washed with 1 M HCl and brine, then dried (MgSO4), filtered and concentrated in vacuo. The crude dioxanone and O-TBS-α-hydroxy amide (0.5 mmol) were dissolved in toluene (2 mL) and stirred at reflux for 1 h. The reaction was cooled to room temperature, concentrated in vacuo and loaded onto a plug of SiO$_2$ and eluted with 10% EtOAc:hexanes (100 mL). The resulting crude imide was dissolved in dichloromethane (2.5 mL) and trifluoroacetic acid (2.5 mL) was added at room temperature. The reaction was allowed to stir for 24 h, was concentrated in vacuo and purified by chromatography on SiO$_2$ (20% EtOAc:hexanes).

(1)

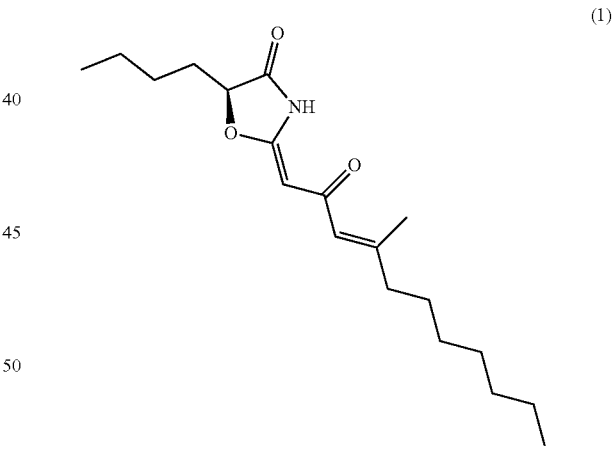

(S)-Lipoxazolidinone A (1). Procedure A. Yield: 6.2 mg (24%) of 1 as a colorless oil: [α]$_D$=−34° (c=0.78, MeOH) [Lit: [α]$_D$=−31° (c=0.02, MeOH)[9]; $^1$H NMR (400 MHz, CDCl$_3$); δ=5.89 (s, 1H), 5.20 (s, 1H), 4.62 (m, 1H), 2.17 (s, 3H), 2.12 (m, 2H), 1.96 (m, 1H), 1.81 (m, 1H), 1.48-1.25 (m, 14H), 0.93-0.86 (m, 6H); $^{13}$C NMR (100 MHz, CDCl$_3$): δ=189.9, 167.0, 158.3, 124.8, 94.9, 84.5, 79.1, 41.9, 32.2, 31.2, 29.7, 29.6, 28.1, 26.6, 23.1, 22.7, 19.6, 14.6, 14.2; IR (film) 2959, 2918, 2884, 1762, 1631, 1557, 1442; HRMS (ESI) m/z calculated for C$_{19}$H$_{31}$NO$_3$ [M+H]$^+$: 322.23767, found: 322.23754.

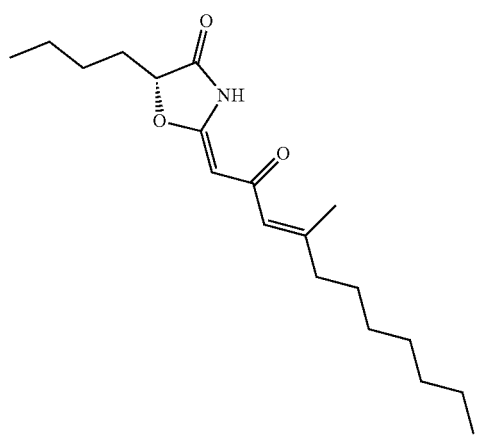

(2)

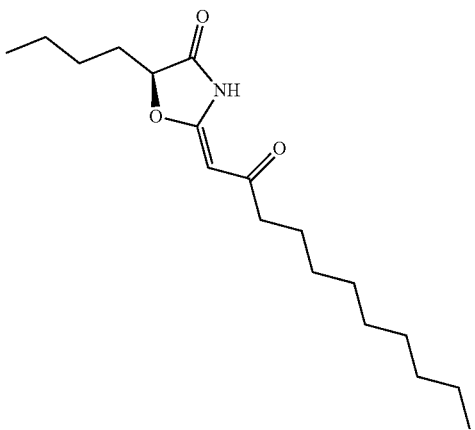

(4)

(R)-Lipoxazolidinone A (2). Procedure A. Yield 2.7 mg (21%) of 2 as a colorless oil: $[\alpha]_D$=+30° (c=0.09, dichloromethane); $^1$H NMR (700 MHz, CDCl$_3$); δ=5.89 (s, 1H), 5.20 (s, 1H), 4.62 (m, 1H), 2.17 (s, 3H), 2.13 (m, 2H), 1.98 (m, 1H), 1.82 (m, 1H), 1.47-1.36 (m, 6H), 1.28 (m, 8H), 0.93-0.87 (m, 6H); $^{13}$C NMR (175 MHz, CDCl$_3$): δ=189.8, 174.0, 166.9, 158.2, 124.6, 84.4, 78.9, 41.8, 32.1, 31.1, 29.6, 29.5, 27.9, 26.5, 23.0, 22.5, 19.5, 14.4, 14.1; FIRMS (ESI) m/z calculated for C$_{19}$H$_{31}$NO$_3$ [M+H]$^+$: 322.23767, found: 322.23806.

(S,E)-5-Butyl-2-(2-oxoundecylidene)oxazolidin-4-one (4). Procedure B. Yield 11 mg (44%) of 4 as a white solid: $[\alpha]_D$=−29° (c=0.25, dichloromethane); $^1$H NMR (400 MHz, CDCl$_3$); δ=5.24 (s, 1H), 4.63 (dd, J=7.4, 4.2 Hz, 1H), 2.35 (t, J=7.1 Hz, 4H), 1.97 (m, 1H), 1.83 (m, 1H), 1.61 (m, 4H), 1.43-1.26 (m, 12H), 0.94-0.86 (m, 6H); $^{13}$C NMR (175 MHz, CDCl$_3$): δ=200.8, 173.3, 165.6, 81.8, 79.0, 43.3, 32.2, 31.1, 31.0, 29.8, 29.7, 29.6, 26.5, 25.6, 23.0, 22.5, 14.4, 14.1; IR (film) 2958, 2924, 2862, 1708, 1670, 1570, 1461; HRMS (ESI) m/z calculated for C$_{18}$H$_{31}$NO$_3$ [M+H]$^+$: 310.23767, found: 310.23771.

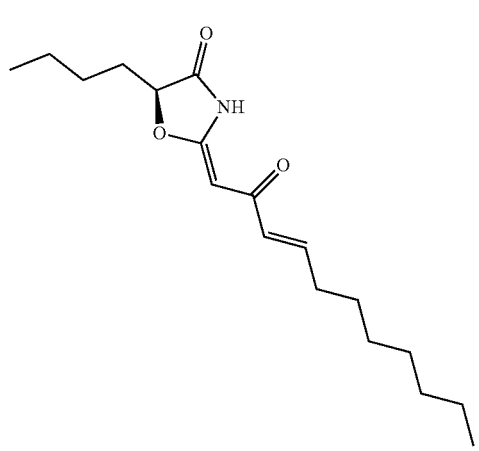

(3)

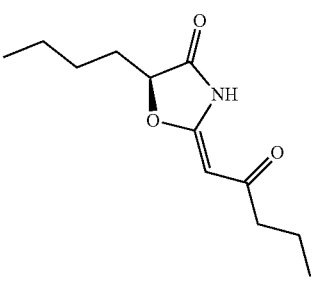

(5)

(S,E)-5-Butyl-2-((E)-2-oxoundec-3-en-1-ylidene)oxazolidin-4-one (3). Procedure A. Yield 6.2 mg (24%) of 3 as a white solid: $[\alpha]_D$=−35° (c=0.49, dichloromethane); $^1$H NMR (400 MHz, CDCl$_3$); δ=6.83 (dt, J=15.8, 6.9 Hz, 1H), 6.09 (d, J=15.1 Hz, 1H), 5.32 (s, 1H), 4.65 (dd, J=6.8, 4.1 Hz, 1H), 2.22 (m, 2H), 1.95 (m, 1H), 1.83 (m, 1H), 1.46-1.34 (m, 6H), 1.27 (m, 8H), 0.94-0.86 (m, 6H); $^{13}$C NMR (175 MHz, CDCl$_3$): δ=188.1, 174.3, 168.0, 146.1, 130.3, 81.7, 79.2, 32.8, 32.1, 31.1, 29.5, 29.4, 28.6, 26.5, 23.0, 22.5, 14.4, 14.1; IR (film) 2958, 2920, 2886, 1768, 1628, 1559, 1441; FIRMS (ESI) m/z calculated for C$_{18}$H$_{29}$NO$_3$ [M+H]$^+$: 308.22202, found: 308.22205.

(S,E)-5-Butyl-2-(2-oxopentylidene)oxazolidin-4-one (5). Procedure B. Yield: 7 mg (39%) of 5 as a white solid: $[\alpha]_D$=−33° (c=0.09, dichloromethane); $^1$H NMR (400 MHz, CDCl$_3$); δ=5.24 (s, 1H), 4.63 (dd, J=7.5, 4.1 Hz, 1H), 2.36 (t, J=7.1 Hz, 2H), 1.99 (m, 1H), 1.82 (m, 1H), 1.65 (m, 2H), 1.39 (m, 4H), 0.97-0.90 (m, 6H); $^{13}$C NMR (175 MHz, CDCl$_3$): δ=200.6, 173.3, 165.7, 81.8, 79.0, 45.2, 31.0, 30.0, 26.5, 22.5, 19.0, 14.1; IR (film) 3182, 2952, 2935, 2861, 1765, 1664, 1568, 1442; HRMS (ESI) m/z calculated for C$_{12}$H$_{19}$NO$_3$ [M+H]$^+$: 226.14377, found: 226.14383.

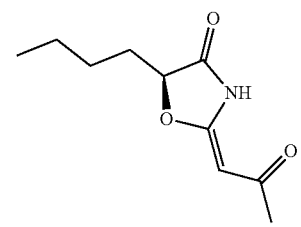

(6)

(S,E)-5-Butyl-2-(2-oxopropylidene)oxazolidin-4-one (6). Procedure A using commercially available dioxanone. Yield 63 mg (72%) of 6 as a white solid: $[\alpha]_D$=−37° (c=0.7, MeOH); $^1$H NMR (400 MHz, CDCl$_3$); δ=5.24 (s, 1H), 4.63 (dd, J=7.4, 4.3 Hz, 1H), 2.15 (s, 3H), 1.96 (m, 1H), 1.82 (m, 1H), 1.38 (m, 4H), 0.92 (t, J=7.1 Hz, 3H); $^{13}$C NMR (175 MHz, CDCl$_3$): δ=197.7, 173.2, 165.5, 82.3, 79.0, 31.0, 30.2, 26.4, 22.5, 14.1; IR (film) 3184, 2957, 2935, 2863, 1767, 1665, 1574, 1431; HRMS (ESI) m/z calculated for C$_{10}$H$_{15}$NO$_3$ [M+H]$^+$: 198.11247, found: 198.11268.

(7)

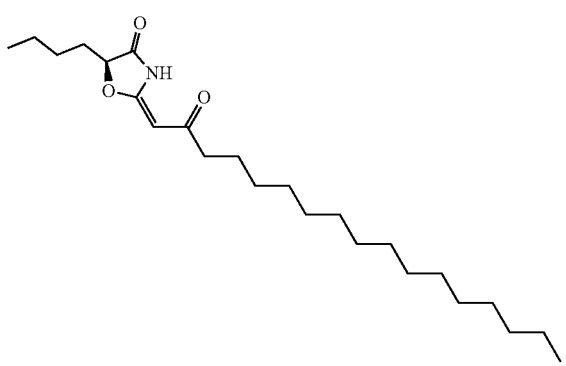

(S,E)-5-Butyl-2-(2-oxoheptadecylidene)oxazolidin-4-one (7). Procedure B. Yield: 14 mg (45%) of 7 as a white solid: R$_f$=0.55 (4:1 hexanes:EtOAc); $[\alpha]_D$=−24° (c=7.9, dichloromethane); $^1$H NMR (400 MHz, CDCl$_3$); δ=5.24 (s, 1H), 4.63 (dd, J=7.5, 4.2 Hz, 1H), 2.34 (m, 4H), 1.95 (m, 1H), 1.85 (m, 1H), 1.63 (m, 4H), 1.45-1.25 (m, 24H), 0.94-0.86 (m, 6H); $^{13}$C NMR (100 MHz, CDCl$_3$): δ=200.8, 179.9, 173.2, 81.6, 78.8, 43.1, 34.2, 32.1, 30.9, 29.9, 29.8, 29.7, 29.7, 29.6, 29.5, 29.4, 29.2, 26.3, 25.5, 24.8, 22.9, 22.3, 14.3, 13.9; IR (film) 2955, 2915, 2848, 1756, 1670, 1468; FIRMS (ESI) m/z calculated for C$_{24}$H$_{43}$NO$_3$ [M+H]$^+$: 394.33157, found: 394.33172.

(8)

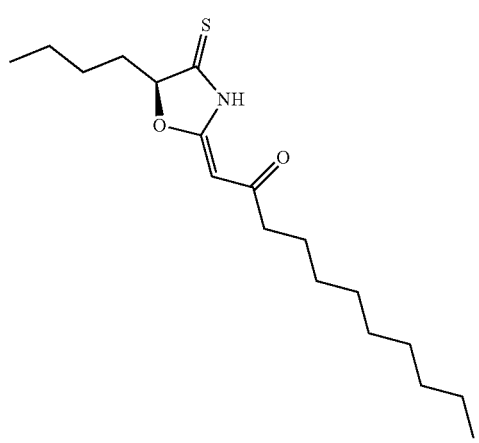

(S,E)-1-(5-butyl-4-thioxooxazolidin-2-ylidene)undecan-2-one (8). Oxazolidinone 4 (12 mg, 0.040 mmol) was dissolved in DCM (0.2 mL) and Lawesson's reagent (8.1 mg, 0.020 mmol) was added. The reaction was stirred for 2 h at room temperature and then concentrated in vacuo and purified by chromatography on SiO$_2$ (10% EtOAc:hexanes) to yield: 9.1 mg (71%) of 8 as a yellow solid: $^1$H NMR (400 MHz, CDCl$_3$); δ=6.19 (s, 1H), 4.67 (dd, J=7.4, 4.5 Hz, 1H), 2.81 (m, 2H), 1.95 (m, 1H), 1.71 (m, 1H), 1.55 (m, 2H), 1.48-1.25 (m, 16H), 0.95-0.86 (m, 6H).

(9)

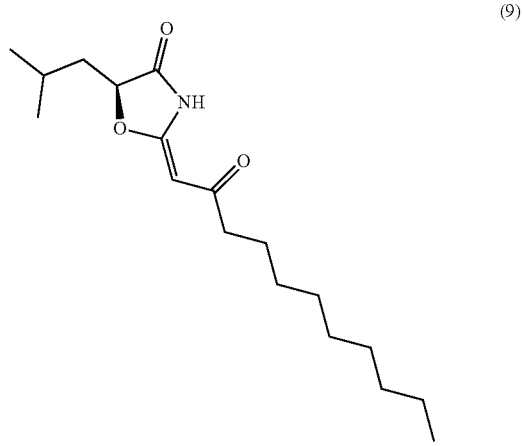 [SMILES: CCCCCCCCCC(=O)/C=C1\NC(=O)[C@H](CC(C)C)O1]

(S,E)-5-isobutyl-2-(2-oxoundecylidene)oxazolidin-4-one (9). Procedure B. Yield: 19 mg (63%) of 9 as a white solid: $^1$H NMR (400 MHz, CDCl$_3$); δ=5.25 (s, 1H), 4.67 (dd, J=9.7, 3.6 Hz, 1H), 2.37 (t, J=7.7 Hz, 2H), 1.90 (m, 1H), 1.81 (m, 1H), 1.70-1.57 (m, 3H), 1.25 (m, 12H), 0.99 (m, 6H), 0.86 (t, J=6.7 Hz, 3H); $^{13}$C NMR (100 MHz, CDCl$_3$): δ=201.4, 173.5, 165.8, 81.9, 77.8, 42.9, 39.9, 32.0, 29.5, 29.4, 29.4, 25.7, 25.0, 23.0, 22.8, 21.8, 14.2; FIRMS (ESI) m/z calculated for C$_{18}$H$_{31}$NO$_3$ [M+H]$^+$: 310.23767, found: 310.23705.

(10)

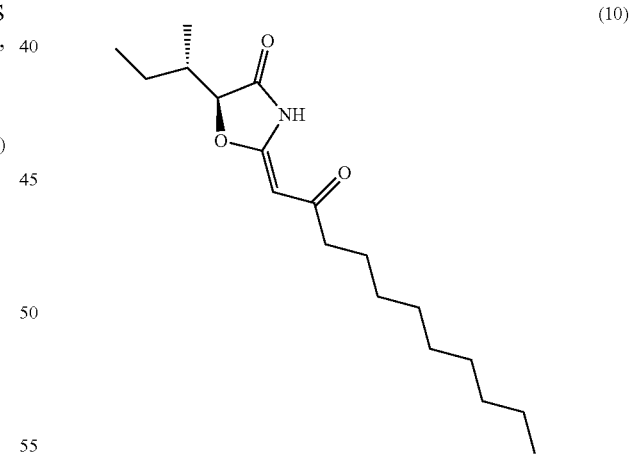

(S,E)-5-((S)-sec-butyl)-2-(2-oxoundecylidene)oxazolidin-4-one (10). Procedure B. Yield: 18 mg (50%) of 10 as a white solid: $^1$H NMR (400 MHz, CDCl$_3$); δ=5.23 (s, 1H), 4.52 (d, J=4.1 Hz, 1H), 2.36 (m, 2H), 2.04 (m, 1H), 1.59 (m, 2H), 1.28 (m, 14H), 1.07 (m, 3H), 0.96-0.85 (m, 6H); $^{13}$C NMR (100 MHz, CDCl$_3$): δ=200.7, 172.4, 165.5, 82.3, 81.3, 43.1, 37.2, 32.0, 29.7, 29.6, 29.5, 29.4, 25.5, 23.3, 22.8, 14.5, 14.3, 11.5; FIRMS (ESI) m/z calculated for C$_{18}$H$_{31}$NO$_3$ [M+H]$^+$: 310.23767, found: 310.23718.

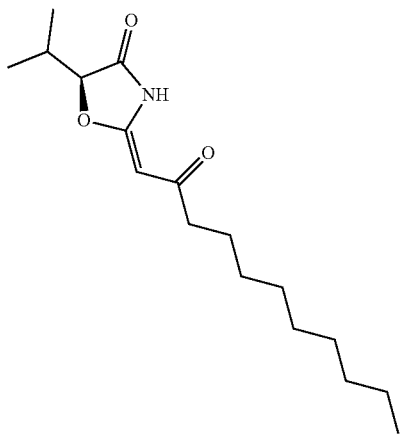

(11)

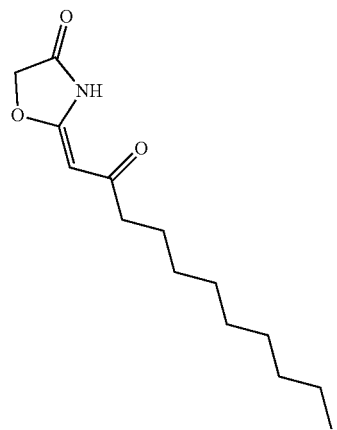

(13)

(S,E)-5-isopropyl-2-(2-oxoundecylidene)oxazolidin-4-one (11). Procedure B. Yield: 33 mg (48%) of 11 as a red/white solid: $^1$H NMR (400 MHz, CDCl$_3$); δ=5.25 (s, 1H), 4.47 (d, J=3.8 Hz, 1H), 2.37 (m, 2H), 2.29 (m, 1H), 1.59 (m, 2H), 1.28 (m, 12H), 1.11 (d, J=7.0 Hz, 3H), 0.97 (d, J=6.9 Hz, 3H) 0.85 (m, 3H); $^{13}$C NMR (100 MHz, CDCl$_3$): δ=201.0, 172.5, 165.7, 82.8, 81.3, 43.1, 32.0, 30.7, 29.6, 29.5, 29.4, 25.5, 22.8, 18.1, 15.7, 14.2; HRMS (ESI) m/z calculated for C$_{17}$H$_{29}$NO$_3$ [M+H]$^+$: 296.22202, found: 296.22188.

(E)-2-(2-Oxoundecylidene)oxazolidin-4-one (13). Procedure B. Yield 19 mg (51%) of 13 as a white solid: $^1$H NMR (400 MHz, CDCl$_3$); δ=5.30 (s, 1H), 4.59 (s, 2H), 2.36 (t, J=7.2 Hz, 2H), 1.62 (m, 2H), 1.26 (m, 12H), 0.87 (t, J=6.8 Hz, 3H); $^{13}$C NMR (175 MHz, CDCl$_3$): δ=200.5, 171.2, 156.9, 82.3, 67.3, 43.2, 34.2, 32.2, 29.8, 29.6, 25.6, 25.0, 23.0, 14.4; IR (film) 2953, 2924, 2868, 1752, 1658, 1442; HRMS (ESI) m/z calculated for C$_{14}$H$_{23}$NO$_3$ [M+H]$^+$: 254.17507, found: 254.17513.

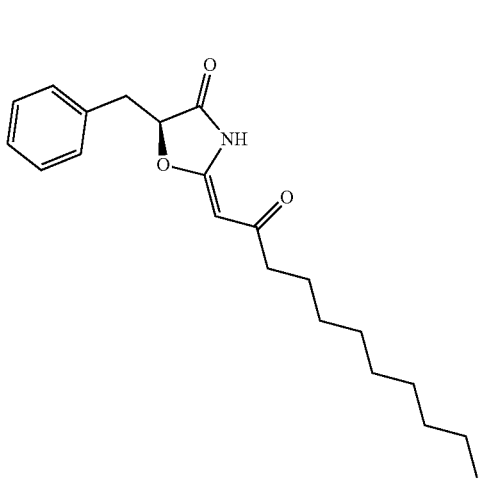

(12)

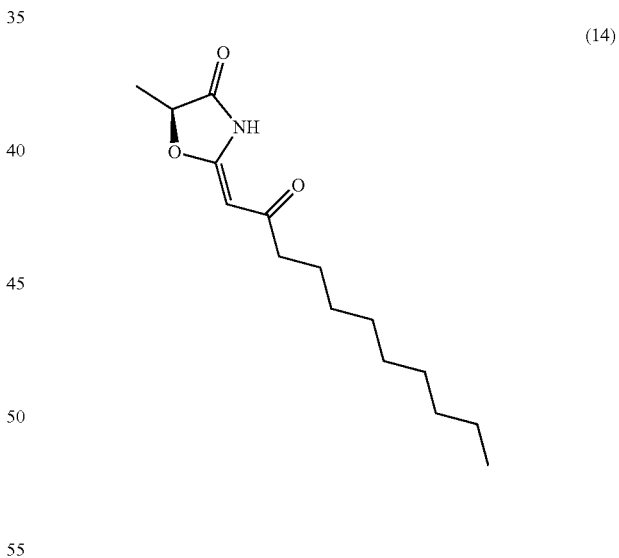

(14)

(S,E)-5-benzyl-2-(2-oxoundecylidene)oxazolidin-4-one (12). Procedure B. Yield: 3.5 mg (17%) of 12 as a white solid: $^1$H NMR (400 MHz, CDCl$_3$); δ=5.20 (s, 1H), 4.87 (dd, J=6.8, 3.9 Hz, 1H), 3.32 (dd, J=14.8, 4.0 Hz, 1H), 3.09 (dd, J=14.8, 6.8 Hz, 1H), 2.35 (t, J=7.7 Hz, 2H), 1.63 (m, 4H), 1.26 (m, 10H), 0.88 (t, J=6.6 Hz, 3H); HRMS (ESI) m/z calculated for C$_{21}$H$_{29}$NO$_3$ [M+H]$^+$: 344.22202, found: 344.22153.

(S,E)-5-Methyl-2-(2-oxoundecylidene)oxazolidin-4-one (14). Procedure B. Yield: 148 mg (46%) of 14 as a white solid: [α]$_D$=−24° (c=7.9, dichloromethane); $^1$H NMR (400 MHz, CDCl$_3$); δ=5.21 (s, 1H), 4.68 (q, J=7.2 Hz, 1H), 2.34 (t, J=6.8 Hz, 2H), 1.56 (m, 5H), 1.25 (m, 12H), 0.85 (t, J=7.1 Hz, 3H); $^{13}$C NMR (100 MHz, CDCl$_3$): δ=200.5, 173.6, 165.0, 81.7, 75.1, 43.0, 32.0, 29.7, 29.5, 29.4, 29.3, 25.4, 22.8, 16.7, 14.2; IR (film) 3220, 3072, 2918, 2848, 1763, 1669, 1576, 1430; HRMS (ESI) m/z calculated for C$_{15}$H$_{25}$NO$_3$ [M+H]$^+$: 268.19072, found: 268.19072.

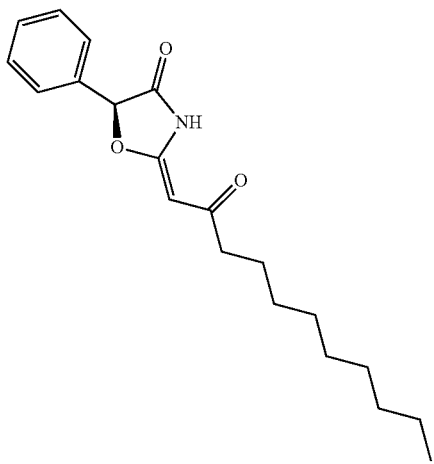

(S,E)-2-(2-oxoundecylidene)-5-phenyloxazolidin-4-one (15). Procedure B. Yield: 7 mg (32%) of 15 as a white solid: ¹H NMR (400 MHz, CDCl₃); δ=7.40 (m, 5H), 5.55 (s, 1H), 5.37 (s, 1H), 2.42 (m, 2H), 1.66 (m, 2H), 1.31 (m, 12H), 0.88 (t, J=6.3 Hz, 3H).

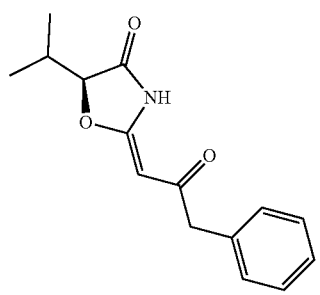

(S,E)-5-isopropyl-2-(2-oxo-3-phenylpropylidene)oxazolidin-4-one (16). Procedure B. Yield: 11 mg (56%) of 16 as an oil: ¹H NMR (400 MHz, CDCl₃); δ=7.34-7.23 (m, 5H), 5.22 (s, 1H), 4.45 (d, J=3.8 Hz, 1H), 3.67 (s, 2H), 2.22 (m, 1H), 1.09 (d, J=7.0 Hz, 3H), 0.95 (d, J=6.9 Hz, 3H); ¹³C NMR (100 MHz, CDCl₃): δ=198.0, 172.3, 166.2, 135.6, 129.7, 129.0, 128.9, 127.6, 127.2, 83.0, 81.2, 50.1, 30.8, 18.2, 15.9.

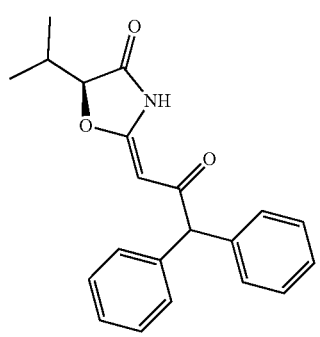

(S,E)-5-isopropyl-2-(2-oxo-3,3-diphenylpropylidene)oxazolidin-4-one (17). Procedure B. Yield: 9.6 mg (46%) of 17 as an oil: ¹H NMR (400 MHz, CDCl₃); δ=7.35-7.24 (m, 10H), 5.07 (s, 1H), 4.46 (d, J=3.9 Hz, 1H), 2.27 (m, 1H), 1.09 (d, J=6.9 Hz, 3H), 0.97 (d, J=6.8 Hz, 3H); ¹³C NMR (100 MHz, CDCl₃): δ=198.7, 172.0, 166.3, 139.4, 129.3, 129.2, 128.8, 127.3, 127.2, 83.0, 82.2, 64.1, 30.7, 18.0, 15.8.

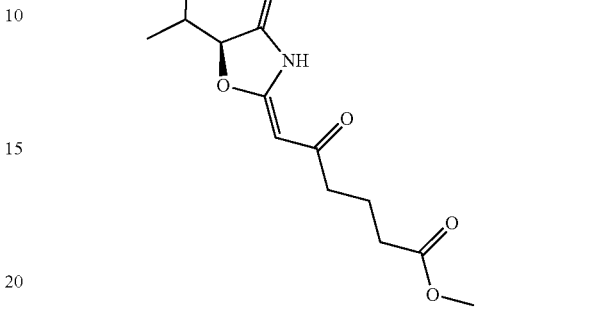

methyl (S,E)-6-(5-isopropyl-4-oxooxazolidin-2-ylidene)-5-oxohexanoate (18). Procedure B. Yield: 12 mg (61%) of 18 as an oil: ¹H NMR (400 MHz, CDCl₃); δ=5.24 (s, 1H), 4.48 (d, J=3.8 Hz, 1H), 3.67 (s, 3H), 2.47-2.27 (m, 5H), 1.94 (m, 2H), 1.11 (d, J=7.0 Hz, 3H), 0.97 (d, J=6.9 Hz, 3H).

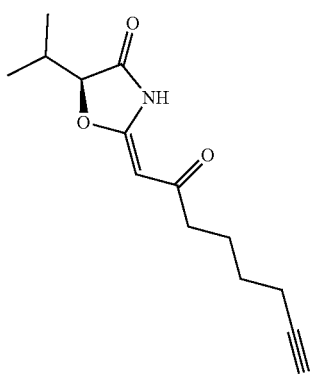

(S,E)-5-isopropyl-2-(2-oxooct-7-yn-1-ylidene)oxazolidin-4-one (19). Procedure B. Yield: 18 mg (55%) of 19 as an oil: ¹H NMR (400 MHz, CDCl₃); δ=5.24 (s, 1H), 4.47 (d, J=3.8 Hz, 1H), 3.74 (s, 1H), 1.95-1.52 (m, 9H), 1.09 (d, J=7.0 Hz, 3H), 0.96 (d, J=6.9 Hz, 3H); ¹³C NMR (100 MHz, CDCl₃): δ=200.0, 172.4, 165.6, 84.0, 82.8, 68.8, 42.31, 33.5, 30.7, 28.1, 27.8, 24.3, 18.3, 18.1.

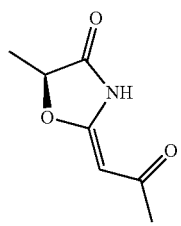

(S,E)-5-methyl-2-(2-oxopropylidene)oxazolidin-4-one (20). Procedure A using commercially available dioxanone.

Yield: 87 mg (56%) of 20 as a white solid. $R_f$=0.27 (50% EtOAc:Hex); $[\alpha]_D$=−28 (c=2.5, DCM); $^1$H NMR (400 MHz, CDCl$_3$); δ=5.22 (s, 1H), 4.70 (q, J=7.0 Hz, 1H), 2.13 (s, 3H), 1.55 (d, J=7.1 Hz, 3H); $^{13}$C NMR (175 MHz, CDCl$_3$): δ=197.6, 173.7, 165.2, 82.5, 75.3, 30.2, 16.9; IR (film) 3186, 2989, 2935, 1761, 1666, 1568; FIRMS (ESI) m/z calculated for C$_7$H$_9$ NO$_3$ [M+H]$^+$: 156.06552, found: 156.06558.

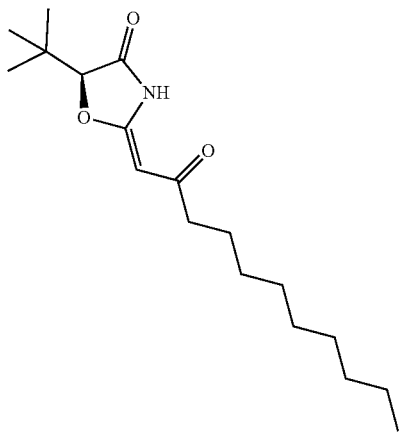

(21)

(S,E)-5-(tert-butyl)-2-(2-oxoundecylidene)oxazolidin-4-one (21). Procedure B. Yield: 9.7 mg (13%) of 21 as a white solid: $^1$H NMR (400 MHz, CDCl$_3$); δ=5.24 (s, 1H), 4.23 (s, 1H), 2.36 (t, J=7.6 Hz, 2H), 1.63-1.56 (m, 2H), 1.32-1.22 (m, 12H), 1.07 (s, 9H), 0.90-0.84 (t, J=6.8 Hz, 3H).

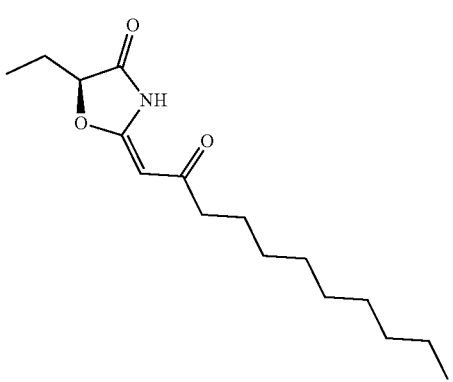

(22)

(S,E)-5-ethyl-2-(2-oxoundecylidene)oxazolidin-4-one (22). Procedure B. Yield: 8.3 mg (18%) of 22 as a white solid: $^1$H NMR (400 MHz, CDCl$_3$); δ=5.24 (s, 1H), 4.61 (dd, J=6.4, 4.6 Hz, 1H), 2.37 (t, J=7.5 Hz, 2H), 2.10-1.96 (m, 1H), 1.92-1.81 (m, 1H), 1.63-1.54 (m, 2H), 1.31-1.21 (m, 12H), 1.02 (t, J=7.4 Hz, 2H), 0.87 (t, J=6.7 Hz, 3H).

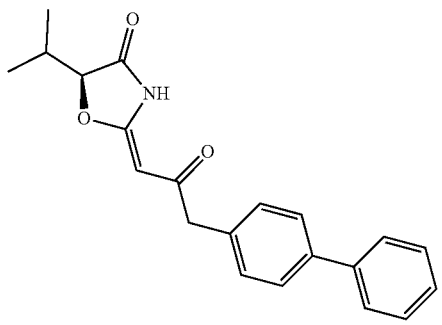

(23)

(S,E)-2-(3-([1,1'-biphenyl]-4-yl)-2-oxopropylidene)-5-isopropyloxazolidin-4-one (23). Procedure B. Yield: 6.8 mg (47%) of 23 as an oil: $^1$H NMR (400 MHz, CDCl$_3$); δ=7.58 (m, 4H), 7.43 (m, 2H), 7.31 (m, 3H), 5.27 (s, 1H), 4.47 (d, J=3.8 Hz, 1H), 3.71 (s, 2H), 2.28 (m, 1H), 1.10 (d, J=7.0 Hz, 3H), 0.97 (d, J=6.9 Hz, 3H).

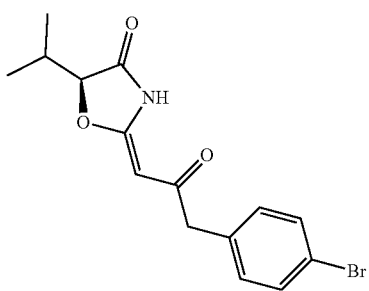

(24)

(S,E)-2-(3-(4-bromophenyl)-2-oxopropylidene)-5-isopropyloxazolidin-4-one (24). Procedure B. Yield: 7.4 mg (51%) of 24 as an oil: $^1$H NMR (400 MHz, CDCl$_3$); δ=7.46 (m, 2H), 7.12 (m, 2H), 5.19 (s, 1H), 4.47 (d, J=3.9 Hz, 1H), 3.61 (s, 2H), 2.28 (m, 1H), 1.09 (d, J=7.0 Hz, 3H), 0.95 (d, J=6.9 Hz, 3H).

Biological Characterization of 4-Oxazolidinones

Broth microdilution protocol for minimum inhibition concentration (MIC) determination. Fresh Mueller-Hinton broth (MHB) ~3 ml, was inoculated ($5\times10^5$ CFU mL$^{-1}$) with MRSA (ATCC 33591) methicillin-resistant *Staphylococcus aureus*. The resulting bacterial suspension was aliquoted (1 mL) into culture tubes and test compound (10 mM DMSO stock solution) was added to reach the final concentration of the interest. Bacteria not treated with the antimicrobial compound served as the control. Rows 2-12 of a 96-well microtiter plate were filled with remaining bacterial subcultures. The samples containing test compound were aliquoted (200 μL) into the first row wells of the microtiter plate (2 wells per compound). Row 1 wells were mixed 6-8 times and 100 μL was transferred down to row 2. Row 2 wells were mixed 6-8 times, followed by a 100 μL transfer from row 2 down to row 3. The rest of the rows of the plate were serially diluted in similar fashion. The plate was covered with sealing tape for 96-well plates (ThermoFisher) and incubated under stationary conditions at 37° C. A duplicate of the plate was prepared. The lowest concentration of test compound at which no visible growth of bacteria occurred—minimum inhibitory concentration (MIC) values were recorded after 16 h.

The results are included in Table 1 below. MIC values for vancomycin, linezolid, and tetracycline are included in Table 1 for purposes of comparison.

TABLE 1

Activity of Compounds 1-24.

| Compound | S. aureus | MRSA | A. baumannii |
|---|---|---|---|
| 1 | 1 | 0.5 | >50 |
| 2 | 4 | 1 | NT |
| 3 | 0.5 | 0.125 | >50 |
| 4 | 2 | 0.25 | NT |
| 5 | 16 | 16 | >50 |
| 6 | 128 | >128 | NT |
| 7 | 128 | 16 | NT |
| 8 | 128 | 64 | NT |
| 9 | 0.5 | 0.0675 | >128 |
| 10 | 0.5 | 0.0675 | >128 |
| 11 | 0.5 | 0.0338 | >64 |
| 12 | 4 | 0.5 | NT |
| 13 | 4 | 2 | NT |
| 14 | 1 | 0.8 | NT |
| 15 | 2 | 1 | >128 |
| 16 | NT | 2 | NT |
| 17 | NT | 0.5 | NT |
| 18 | NT | 32 | NT |
| 19 | NT | 16 | NT |
| 20 | >128 | >128 | NT |
| 21 | 0.5 | 0.0675 | NT |
| 22 | 2 | 1 | NT |
| 23 | 0.25 | 0.125 | NT |
| 24 | 1 | 0.5 | NT |
| vancomycin | 1 | 1 | >100 |
| linezolid | 0.5 | 1 | >100 |
| tetracycline | 0.25 | NT | 2 |

The compounds, compositions, and methods of the appended claims are not limited in scope by the specific compounds, compositions, and methods described herein, which are intended as illustrations of a few aspects of the claims. Any compounds, compositions, and methods that are functionally equivalent are intended to fall within the scope of the claims. Various modifications of the compounds, compositions, and methods in addition to those shown and described herein are intended to fall within the scope of the appended claims. Further, while only certain representative compounds, compositions, and method steps disclosed herein are specifically described, other combinations of the compounds, compositions, and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than where noted, all numbers expressing geometries, dimensions, and so forth used in the specification and claims are to be understood at the very least, and not as an attempt to limit the application of the doctrine of equivalents to the scope of the claims, to be construed in light of the number of significant digits and ordinary rounding approaches.

Unless defined otherwise, all technical and scientific terms used herein have the same meanings as commonly understood by one of skill in the art to which the disclosed invention belongs. Publications cited herein and the materials for which they are cited are specifically incorporated by reference.

What is claimed is:

1. A compound defined by Formula I

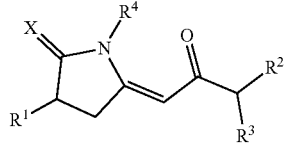

Formula I or a pharmaceutically acceptable salt or prodrug thereof, wherein
X is O;
$R^1$ is chosen from alkyl, cycloalkyl, and alkylcycloalkyl each optionally substituted with one or more substituents individually chosen from $R^5$;
$R^2$ is chosen from alkyl, haloalkyl, aryl, cycloalkyl, alkylaryl, and alkylcycloalkyl, each optionally substituted with one or more substituents individually chosen from $R^5$;
$R^3$ is hydrogen;
$R^4$ is hydrogen; and
$R^5$ is chosen from hydroxy, halogen, —CN, —NO$_2$, amino, alkylamino, dialkylamino, alkyl, haloalkyl; alkylthio; haloalkylthio; alkoxy, haloalkoxy, alkenyl, haloalkenyl, alkynyl, haloalkynyl, aryl, heteroaryl, cycloalkyl, cycloheteroalkyl, alkylaryl, alkylheteroaryl, alkylcycloalkyl, alkylcycloheteroalkyl, alkylsulfinyl, haloalkylsulfinyl, alkylsulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, dialkylaminocarbonyl, and heterodialkylaminocarbonyl.

2. The compound of claim 1, wherein $R^1$ is a $C_1$-$C_4$ alkyl group.

3. The compound of claim 2, wherein $R^1$ is a branched $C_3$-$C_4$ alkyl group.

4. The compound of claim 3, wherein $R^1$ is an isopropyl group.

5. The compound of claim 1, wherein the compound is defined by Formula II

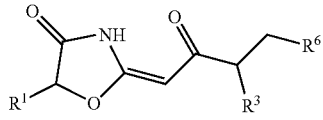

Formula II or a pharmaceutically acceptable salt or prodrug thereof, wherein
$R^1$ is chosen from alkyl, cycloalkyl, and alkylcycloalkyl, each optionally substituted with one or more substituents individually chosen from $R^5$;
$R^3$ is hydrogen;
$R^6$ is chosen from hydrogen, alkyl, haloalkyl, aryl, cycloalkyl, alkylaryl, alkylcycloalkyl, each optionally substituted with one or more substituents individually chosen from $R^5$; and $R^5$ is chosen from hydroxy, halogen, —CN, —NO$_2$, amino, alkylamino, dialkylamino, alkyl, haloalkyl; alkylthio; haloalkylthio; alkoxy, haloalkoxy, alkenyl, haloalkenyl, alkynyl, haloalkynyl, aryl, heteroaryl, cycloalkyl, cycloheteroalkyl, alkylaryl, alkylheteroaryl, alkylcycloalkyl, alkylcycloheteroalkyl, alkylsulfinyl, haloalkylsulfinyl, alkylsulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, dialkylaminocarbonyl, and heterodialkylaminocarbonyl.

6. The compound of claim 5, wherein $R^6$ comprises a $C_1$-$C_8$ alkyl group.

7. The compound of claim 1, wherein the compound is defined by Formula III

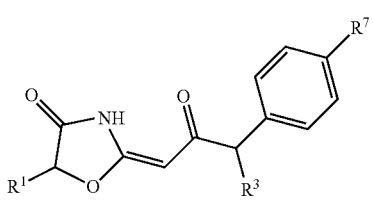

Formula III or a pharmaceutically acceptable salt or prodrug thereof, wherein $R^1$ is chosen from alkyl, cycloalkyl, and alkylcycloalkyl;

$R^3$ is hydrogen;

$R^7$ is chosen from hydrogen, halogen, hydroxyl, —CN, —NO$_2$, amino, alkylamino, dialkylamino, alkyl, haloalkyl, alkenyl, haloalkenyl, alkynyl, haloalkynyl, alkylthio, haloalkylthio, alkoxy, haloalkoxy, aryl, heteroaryl, cycloalkyl, cycloheteroalkyl, alkylaryl, alkylheteroaryl, alkylcycloalkyl, alkylcycloheteroalkyl alkylsulfinyl, haloalkylsulfinyl, alkyl sulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, dialkylaminocarbonyl, and heterodialkylaminocarbonyl, each optionally substituted with one or more substituents individually chosen from $R^5$; and $R^5$ is chosen from hydroxy, halogen, —CN, —NO$_2$, amino, alkylamino, dialkylamino, alkyl, haloalkyl; alkylthio; haloalkylthio; alkoxy, haloalkoxy, alkenyl, haloalkenyl, alkynyl, haloalkynyl, aryl, heteroaryl, cycloalkyl, cycloheteroalkyl, alkylaryl, alkylheteroaryl, alkylcycloalkyl, alkylcycloheteroalkyl, alkylsulfinyl, haloalkylsulfinyl, alkylsulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, dialkylaminocarbonyl, and heterodialkylaminocarbonyl.

8. A biofilm preventing, removing, or inhibiting composition comprising a carrier and an effective amount of a compound defined by claim 1.

9. A method of treating a subject infected with a bacterium comprising administering to the subject a therapeutically effective amount of a compound of claim 1.

10. A method of controlling biofilm formation on a substrate comprising contacting the substrate with a compound defined by claim 1 in an amount effective to inhibit biofilm formation.

11. A medical device comprising:
(a) a medical device substrate; and
(b) an effective amount of a compound of claim 1, either coating the substrate, or incorporated into the substrate, wherein said effective amount of said compound prevents or inhibits the growth of a biofilm thereon.

\* \* \* \* \*